(12) United States Patent
Zedayko et al.

(10) Patent No.: US 11,763,920 B2
(45) Date of Patent: Sep. 19, 2023

(54) MUCUS ANALYSIS FOR ANIMAL HEALTH ASSESSMENTS

(71) Applicant: DIG LABS CORPORATION, Lebanon, NJ (US)

(72) Inventors: Tara Courtney Zedayko, Ringoes, NJ (US); Vamshi Kumar Bogoju, Columbus, OH (US)

(73) Assignee: DIG LABS CORPORATION, Lebanon, NJ (US)

( * ) Notice: Subject to any disclaimer, the term of this patent is extended or adjusted under 35 U.S.C. 154(b) by 189 days.

(21) Appl. No.: 17/160,581

(22) Filed: Jan. 28, 2021

(65) Prior Publication Data

US 2021/0151137 A1 May 20, 2021

Related U.S. Application Data

(63) Continuation-in-part of application No. 16/945,009, filed on Jul. 31, 2020.
(Continued)

(51) Int. Cl.
*G16H 10/20* (2018.01)
*G16H 15/00* (2018.01)
(Continued)

(52) U.S. Cl.
CPC ............ *G16H 10/20* (2018.01); *G16H 15/00* (2018.01); *G16H 20/30* (2018.01); *G16H 20/60* (2018.01); *G16H 50/20* (2018.01)

(58) Field of Classification Search
CPC .......... G06T 7/0012; G06T 7/40; G06T 7/62; G06T 7/09; G06T 2207/20084;
(Continued)

(56) References Cited

U.S. PATENT DOCUMENTS

| 5,968,569 A | 10/1999 | Cavadini et al. |
| 6,861,053 B1 | 3/2005 | Lin et al. |

(Continued)

FOREIGN PATENT DOCUMENTS

| CN | 104152375 B | 8/2016 |
| CN | 107542136 A | 1/2018 |

(Continued)

OTHER PUBLICATIONS

USPTO, U.S. Appl. No. 16/945,009, Non-Final Office Action dated Oct. 27, 2022, 14 pages.
(Continued)

*Primary Examiner* — Tom Y Lu
(74) *Attorney, Agent, or Firm* — Bass Patent Law, LLC

(57) ABSTRACT

The present teachings generally include techniques for characterizing the health of an animal (e.g., gastrointestinal health) using image analysis (e.g., of a sample of an exudate such as mucus) as a complement, alternative, or a replacement to traditional laboratory analyses of biological specimens. The present teachings may further include techniques for personalizing a health and wellness plan (including, but not limited to, a dietary supplement such as a customized formula based on a health assessment), where such a plan may be based on one or more of the health characterization techniques described herein. The present teachings may also or instead include techniques or plans for continuous care for an animal, e.g., by executing health characterization and heath planning techniques in a cyclical fashion. A personalized supplement system (e.g., using a personalized supplement, personalized dosing device, and personalized packaging) may also or instead be created using the present teachings.

20 Claims, 15 Drawing Sheets

Related U.S. Application Data

(60) Provisional application No. 62/880,836, filed on Jul. 31, 2019.

(51) Int. Cl.
*G16H 20/30* (2018.01)
*G16H 50/20* (2018.01)
*G16H 20/60* (2018.01)

(58) Field of Classification Search
CPC ........ G06T 2207/30004; A61B 5/0013; A61B 5/42; A61B 5/483; A61B 5/7275; A61B 2503/40; G16H 15/00; G16H 20/30; G16H 20/60; G16H 20/70; G16H 40/67; G16H 50/20; G16H 30/02; G16H 50/30; G16H 50/50; G06N 3/08; G06N 20/00
See application file for complete search history.

(56) References Cited

U.S. PATENT DOCUMENTS

| | | | |
|---|---|---|---|
| 8,762,167 B2 | 6/2014 | Blander et al. | |
| 9,433,651 B2 | 9/2016 | Jones et al. | |
| 9,703,929 B2 | 7/2017 | Apte et al. | |
| 10,194,685 B2 | 2/2019 | Delaney | |
| 10,287,639 B2 | 5/2019 | Apte et al. | |
| 10,930,401 B2 | 2/2021 | Olives et al. | |
| 2003/0212574 A1 | 11/2003 | Olivier | |
| 2006/0051873 A1 | 3/2006 | Fitzgerald | |
| 2006/0099310 A1 | 5/2006 | Koekkoek | |
| 2009/0006127 A1 | 1/2009 | Bahar | |
| 2011/0014351 A1 | 1/2011 | Reider et al. | |
| 2013/0052624 A1 | 2/2013 | Saps et al. | |
| 2014/0272028 A1 | 9/2014 | Donavon et al. | |
| 2017/0148348 A1 | 5/2017 | Hardee et al. | |
| 2017/0156386 A1 | 6/2017 | Baetge et al. | |
| 2017/0303901 A1 | 10/2017 | Sekine | |
| 2018/0030466 A1 | 2/2018 | Ronen et al. | |
| 2018/0211380 A1* | 7/2018 | Tandon | G06K 9/6271 |
| 2018/0303466 A1 | 10/2018 | Kashyap et al. | |
| 2018/0322660 A1 | 11/2018 | Smith | |
| 2020/0103406 A1 | 4/2020 | Holmes et al. | |
| 2021/0035289 A1 | 2/2021 | Zedayko et al. | |
| 2021/0386367 A1* | 12/2021 | Wahl | A61B 5/42 |

FOREIGN PATENT DOCUMENTS

| | | |
|---|---|---|
| CN | 105574899 B | 8/2018 |
| WO | 2006116296 A3 | 11/2006 |
| WO | 2011008950 A2 | 1/2011 |
| WO | 2014069896 A1 | 5/2014 |
| WO | 2015176994 A1 | 11/2015 |
| WO | 2017138007 | 8/2017 |
| WO | 2018187790 A2 | 10/2018 |
| WO | 2019232295 A1 | 12/2019 |
| WO | 2021022162 | 2/2021 |
| WO | 2022025982 | 2/2022 |

OTHER PUBLICATIONS

Bouatra, Souhaila, et al. "The Human Urine Metabolome", Plos One, vol. 8, No. 9, Sep. 4, 2013, e73076, XP055401320, DOI: 10.1371/journal.pone.0073076, pp. 1-28.

EPO, "The International Search Report and The Written Opinion of the International Searching Authority" dated Oct. 27, 2020. 15 pages.

International Searching Authority/U.S., PCT Application No. PCT/US21/15382, "International Search Report and Written Opinion" dated Jun. 1, 2021, 13 Pages.

ISA/EPO, "PCT International Preliminary Report on Patentability" PCT/US20/44507, dated Feb. 10, 2022 11 pages.

USPTO, U.S. Appl. No. 16/945,009, Non-Final Office Action dated May 10, 2023, 10 pages.

USPTO, "U.S. Appl. No. 16/945,009, Final Office Action dated Feb. 9, 2023," 10 pages.

* cited by examiner

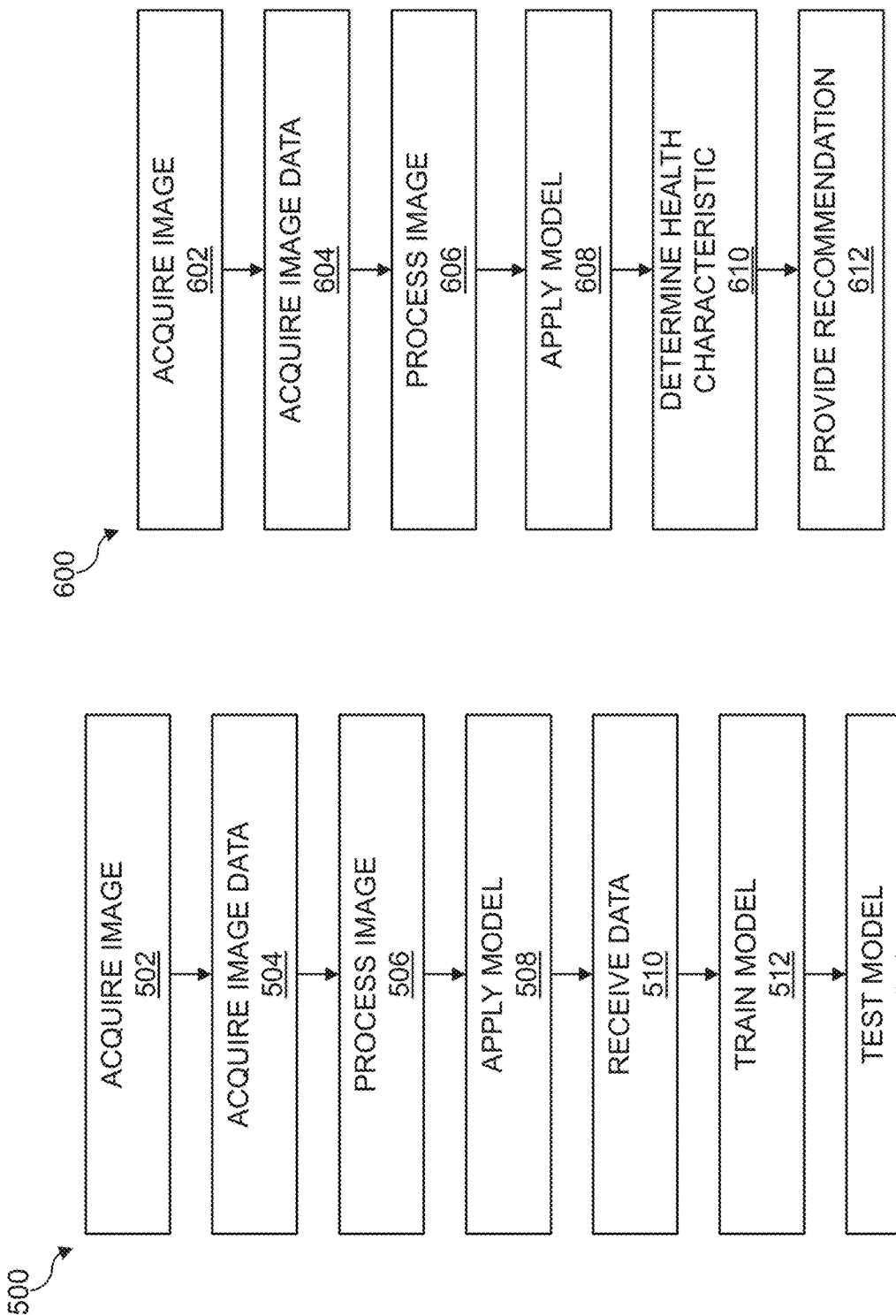

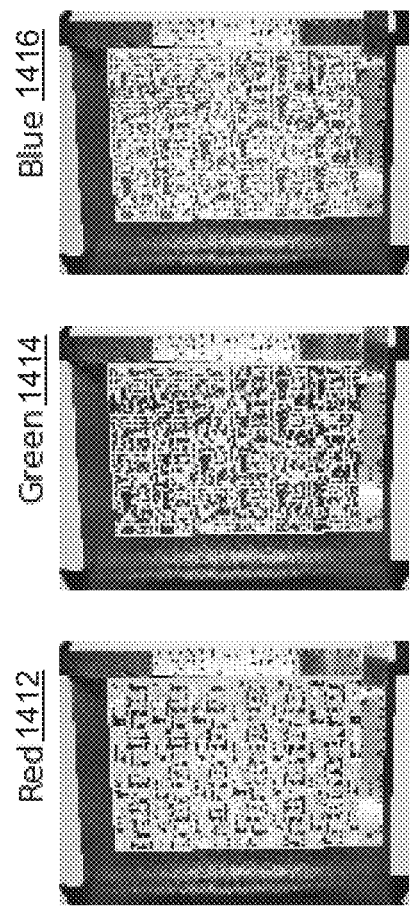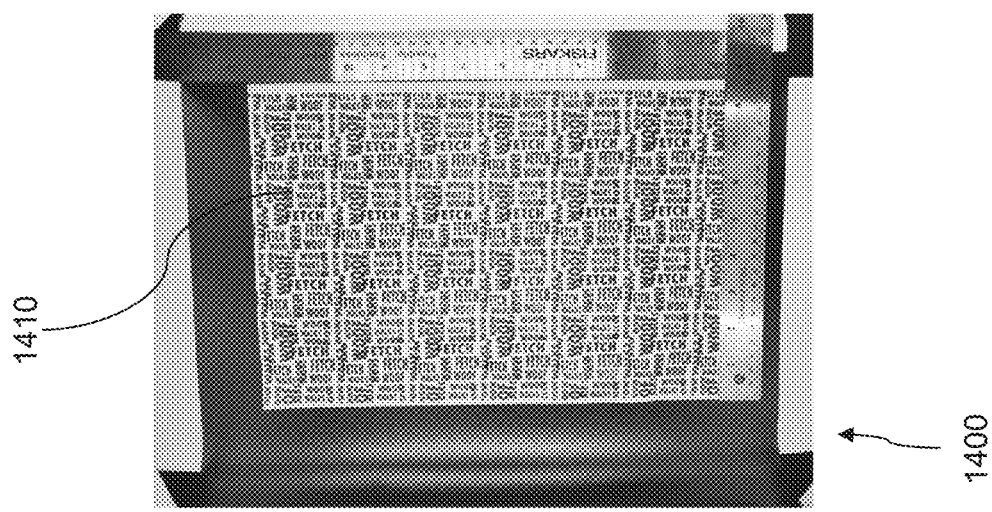
FIG. 14

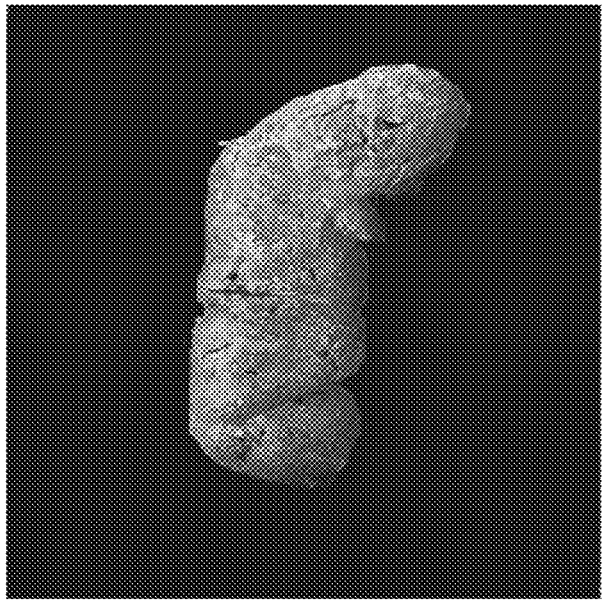
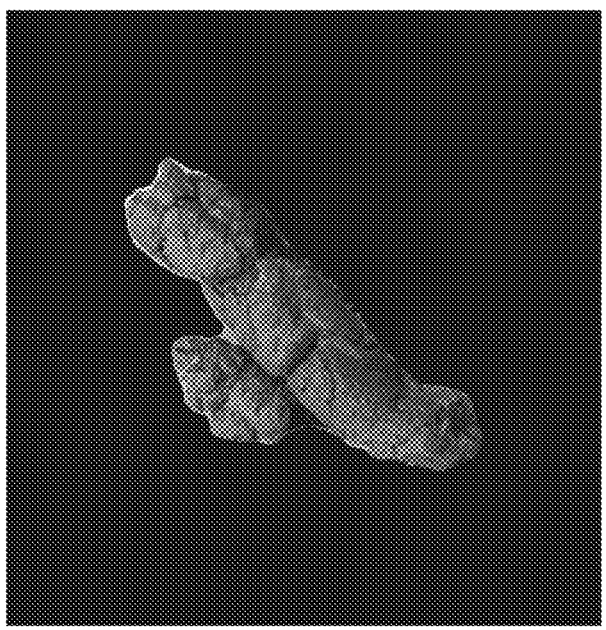
FIG. 15

MUCUS ANALYSIS FOR ANIMAL HEALTH ASSESSMENTS

CROSS-REFERENCE TO RELATED APPLICATIONS

This application is a continuation-in-part of U.S. patent application Ser. No. 16/945,009 filed on Jul. 31, 2020, which claims priority to U.S. Provisional Patent Application No. 62/880,836 filed on Jul. 31, 2019, where the entire contents of each of the foregoing applications are incorporated by reference herein.

This application is also related to Int'l Pat. App. No. PCT/US20/44507 filed on Jul. 31, 2020, which claims priority to U.S. Provisional Patent Application No. 62/880,836 filed on Jul. 31, 2019, where the entire contents of each of the foregoing applications are incorporated by reference herein.

FIELD

The present disclosure generally relates to techniques for assessing animal health—e.g., through analysis of an image of a biological sample such as mucus—and techniques for creating personalized systems for the animal.

BACKGROUND

The digestive tract of humans and other animals is covered on the inside by epithelium containing mucus-secreting goblet cells. Mucus possesses important protective, physical, and immune functions. The stomach and small intestine are lined with a single-layer mucus coating, while the large intestine has two-layered mucus coating. The functions of these mucus coatings can vary greatly based on location and layer. Recent research demonstrates the capability of mucus to possess both antibacterial and bacteria binding properties. Furthermore, comprising over 99% to 99.99% water, the physical properties of mucus can help inhibit bacterial passage through to the fragile epithelium via physical size restrictions and by inhibiting mobility with its gel-like properties.

Because of its extremely high water content, and fragile chemical structure and composition, mucus itself can be an extremely fragile and fleeting substance. Therefore, the study and research of mucus as a substance poses real technical challenges. It is generally accepted that we are still only at the beginning of understanding the function and importance of the mucus layer (see, e.g., Gastroenterology Report 7(1), 2019, pp. 3-12, which is incorporated by reference herein in its entirety). Further, because over 70% of an animal's immunity lives in the gastrointestinal tract, mucus therefore can play a pivotal role as the literal gatekeeper to the host organism—e.g., by selectively allowing and denying exposure to critical metabolites, including vitamins and short-chain fatty acids, which are critical for host animal health and nutrition. And because each animal's life is unique and the mucus properties are challenging to assess in a laboratory setting, there exist significant challenges when attempting to use mucus to assess animal health and determine treatment or other courses of action for an animal. Further, most diagnostic and detection methods to assess animal health are built on traditional exudates, including stool, blood, or urine.

Currently, for example, animal health assessment may include submission of a physical sample of an animal's stool or questionnaire responses related to health, behavior, current diet, and other ethnographic information, where this information is then analyzed and compared to a reference database in order to provide a personalized health plan. These techniques can require intricate and complicated steps that often take several weeks (or months) to process, which is often a major barrier to collecting a reliable sample and diagnosing in sufficient time to provide a viable solution for a particular animal. These assessments are also lacking the means to assess a fleeting exudate—like mucus—in a standardized fashion, to provide or to enhance a real-time health assessment.

There remains a need for improvements in animal health assessment, e.g., utilizing more real-time presentations of animal specimens such as mucus and the like for generating more accurate results and more efficient recommendations or treatment plans.

SUMMARY

The present teachings generally include techniques for characterizing the health of an animal (e.g., gastrointestinal health) using image analysis (e.g., of a sample of an exudate such as mucus) as a complement, alternative, or a replacement to traditional laboratory analyses of biological specimens. The present teachings may also or instead include techniques for personalizing a health and wellness plan (including, but not limited to, a dietary supplement such as a customized formula based on a health assessment), where such a health and wellness plan may be based on one or more of the health characterization techniques described herein. The present teachings may also or instead include techniques or plans for continuous care for an animal, e.g., by executing health characterization and heath planning techniques in a cyclical fashion. A personalized supplement system (e.g., using a personalized supplement, personalized dosing device, and personalized packaging) may also or instead be created using the present teachings.

In an aspect, a method of analyzing an image of a biological sample to provide a health assessment of an animal may include: receiving an image, the image including a biological sample containing mucus; identifying and extracting one or more regions of interest within the image for further analysis; applying a model to the one or more regions of interest to identify one or more conditions of mucus therein, the model trained using a plurality of images having varying conditions of mucus, where output of the model includes at least a grade corresponding to an amount of mucus present in the one or more regions of interest; based at least in part on the output of the model, predicting a health characteristic of an animal from which the biological sample originated; and presenting the health characteristic to a user associated with the animal.

Implementations may include one or more of the following. The method may further include providing a treatment for the animal in view of the health characteristic. The treatment may include a customized health plan for the animal. The customized health plan may include one or more of a behavioral change and a dietary change. The customized health plan may include a recommendation regarding one or more of diet, sleep, exercise, and an activity. The treatment may include one or more of a food, a supplement, and a medicine. The treatment may include a personalized dietary supplement for the animal. The personalized dietary supplement may include a predetermined amount of one or more of a probiotic, a prebiotic, a digestive enzyme, an anti-inflammatory, a natural extract, a vitamin, a mineral, an amino acid, a short-chain fatty acid, an oil, and a formulating agent. The personalized dietary supplement may include one or more of slippery elm bark powder and marshmallow root powder. The method may further include analyzing the health characteristic in view of a reference database to determine the treatment. The method may further include providing a report for the animal that includes the health characteristic. A descriptor may be provided to the user accompanying the health characteristic. An alert may be provided to the user in view of the health characteristic. The grade may identify the amount of mucus as one of absent, low, or high. Output of the model may further include one or more labels corresponding to an opacity of mucus present in the one or more regions of interest. Output of the model may further include one or more labels corresponding to a thickness of mucus present in the one or more regions of interest. Output of the model may further include one or more labels corresponding to a surface area occupied by mucus in the one or more regions of interest. Output of the model may further include one or more labels corresponding to a color of mucus present in the one or more regions of interest. Output of the model may further include one or more labels corresponding to an estimate of microbial content of mucus present in the one or more regions of interest. Output of the model may further include one or more labels corresponding to an estimate of a level of one or more of bacteria and cortisol in the animal. Output of the model may further include one or more labels corresponding to detection of one or more of blood and a pathogen. The model may be a convolutional neural network (CNN) model. The biological sample may be a mucus sample accompanied by a stool sample. The method may further include calculating one or more of a geometric attribute, a texture attribute, and a color attribute within the one or more regions of interest to identify one or more features of the stool sample. The method may further include applying a second model to the one or more features of the stool sample, the second model predicting a second health characteristic of the animal based on the one or more features. The method may further include providing a treatment in view of a combination of the health characteristic and the second health characteristic. The second health characteristic may include a classification on the Bristol stool scale. The second model may include one or more of a machine-learning model and a probabilistic model. One or more features of the stool sample may include at least one of a color, a texture, a number of binaries, an area, a perimeter, a circularity, a mass, an eccentricity, a major axis, a minor axis, a viscosity, a consistency, a moisture content, a solidity, an extent, an equivalent diameter, a specularity, a coherence, a reflectance, a diffusivity, and a presence of a non-stool substance. The image may include metadata. The metadata may include one or more of a time, a date, and a geographic location. The image may be stored in a remote database. Receiving the image may include retrieving the image from the remote database. The method may further include receiving metadata associated with the image. The metadata may include a questionnaire response related to one or more of a health, a behavior, a current diet, a supplement, a medication, ethnographic information, a breed, a weight of the animal, a weight of the biological sample, DNA gene sequencing (of either the host organism and/or the gastrointestinal microflora (also known as microbiome)), and a size of the animal. The metadata may include one or more of geolocation information and physiological information. The metadata may include a ground truth attribute. The metadata may include historical data. The biological sample may include one or more of phlegm, snot, urine, vomit, bile, blood, vaginal discharge, semen, and other biological discharge. Extracting one or more regions of interest may include a segmentation of the image performed at least in part by the model. Extracting one or more regions of interest may include an automatic segmentation of the image. The automatic segmentation may include utilizing one or more semantic segmentation models using deep learning. The method may further include normalizing the one or more regions of interest to account for image variability, thereby creating a normalized image for further standardized analysis. Normalizing one or more regions of interest may account for one or more image acquisition settings used in capturing the image. One or more image acquisition settings may include one or more of a focal length, a color setting, a lighting setting, and a magnification. Normalizing one or more regions of interest may include a resizing of the one or more regions of interest. The method may further include analyzing the output of the model in view of a reference database to determine one or more of the health characteristic and a treatment. The reference database may be a historical database including data from analyses of other biological samples. At least one of the other biological samples may be from the animal. The other biological samples may be from animals distinct from the animal from which the biological sample originated. The image may further include a resting surface having markings thereon, the markings including one or more of a known size, a known shape, and a known color, where the markings are used by the model for analyzing the biological sample.

In an aspect, a computer program product for analyzing an image of a biological sample to provide a health assessment of an animal may include computer executable code embodied in a non-transitory computer readable medium that, when executing on one or more computing devices, performs the steps of: receiving an image, the image including a biological sample containing mucus; identifying and extracting one or more regions of interest within the image for further analysis; applying a model to the one or more regions of interest to identify one or more conditions of mucus therein, the model trained using a plurality of images having varying conditions of mucus, where output of the model includes at least a grade corresponding to an amount of mucus present in the one or more regions of interest; based at least in part on the output of the model, predicting a health characteristic of an animal from which the biological sample originated; and presenting the health characteristic to a user associated with the animal.

In an aspect, a system for analyzing an image of a biological sample to provide a health assessment of an animal may include a data network, a user device coupled to the data network, and a remote computing resource coupled to the data network and accessible to the user device through the data network. The remote computing resource may include a processor and a memory, the memory storing code executable by the processor to perform the steps of: receiving an image from the user device over the data network, the image including a biological sample containing mucus; identifying and extracting one or more regions of interest within the image for further analysis; applying a model to the one or more regions of interest to identify one or more conditions of mucus therein, the model trained using a plurality of images having varying conditions of mucus, where output of the model includes at least a grade corresponding to an amount of mucus present in the one or more regions of interest; based at least in part on the output of the model, predicting a health characteristic of an animal from which the biological sample originated; and presenting the health characteristic on the user device. The code may be further configured to perform the step of transmitting a treatment to the user device over the data network in view of the health characteristic.

In an aspect, a method of formulating a personalized product for an animal may include: receiving an image, the image including a biological sample containing mucus; applying a model to the image to identify one or more conditions of mucus therein, the model trained using a plurality of images having varying conditions of mucus, where output of the model includes at least a grade corresponding to an amount of mucus present; and, based at least in part on the output of the model, selecting one or more ingredients of a personalized product for an animal from which the biological sample originated.

Implementations may include one or more of the following. The method may further include combining one or more ingredients to form the personalized product. The method may further include packaging the personalized product. The method may further include distributing the personalized product to one or more of the animal and a user associated with the animal. The method may further include dosing the personalized product for the animal. The personalized product may include a personalized dietary product. The personalized dietary product may include one or more of a food, a supplement, and a medicine. The personalized product may include one or more of a grooming product, a shampoo, a conditioner, a lotion, a cream, a medicine, an ear drop, an eye drop, a topical substance, a toothpaste, and an oral rinse.

In an aspect, a personalized product may include one or more ingredients derived from a computer-based analysis of mucus in a biological sample extracted from a model applied to an image including the biological sample.

Implementations may include one or more of the following. The biological sample may be stool, where the personalized product includes a personalized dietary product. One or more ingredients may include a predetermined amount of one or more of a probiotic, a prebiotic, a digestive enzyme, an anti-inflammatory, a natural extract, a vitamin, a mineral, an amino acid, a short-chain fatty acid, an oil, and a formulating agent.

In an aspect, a method may include: receiving a plurality of images of biological samples containing varying amounts of mucus; analyzing the plurality of images of biological samples; assigning, for each of the plurality of images, one of a number of grades associated with an amount of mucus present on biological samples contained therein; creating a scale that includes each grade of the number of grades; and inputting the scale into a model programmed to perform an image analysis on an input image, where an output of the model in the image analysis is one of the number of grades.

Implementations may include one or more of the following. The method may further include inputting the input image into the model, and receiving the output including one of the number of grades for the input image. The method may further include training the model by reviewing the output and adjusting the model when the output does not match an expected output. The biological samples in the plurality of images may each include a stool sample. The varying amounts of mucus may range from an absence of mucus to a large amount of mucus defined by an occupation of more than 25 percent of a biological sample. The number of grades may correspond to at least a first condition where mucus is undetected from a biological sample in at least one of the plurality of images, a second condition where mucus is detected but occupies less than a predetermined amount of a biological sample in at least one of the plurality of images, and a third condition having mucus that occupies more than the predetermined amount of a biological sample in at least one of the plurality of images. The first condition may include a grade of 'absent,' the second condition may include a grade of 'low,' and the third condition may include a grade of 'high.' The predetermined amount may be a coating of 25 percent of the biological sample. The predetermined amount may be a coating of 50 percent of the biological sample. A grade in the number of grades may account for one or more of an opacity of mucus, a thickness of mucus, a surface area occupied by mucus, a color of mucus, an estimate of microbial content of mucus, an estimate of a level of cortisol in an animal, and an estimate of a level of bacteria in mucus. The method may further include: receiving a first image including a first biological sample; identifying and extracting one or more regions of interest within the first image for further analysis; applying the model to the one or more regions of interest to identify one or more conditions of mucus therein; receiving output of the model for the first image, the output including at least a first grade of the number of grades; based at least in part on the first grade, predicting a health characteristic of an animal from which the first biological sample originated; and presenting the health characteristic to a user associated with the animal. The method may further include providing a treatment for the animal in view of one or more of the health characteristic and the first grade.

These and other features, aspects, and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

FIG. 5 is a flow chart of a method for training a model, in accordance with a representative embodiment.

FIG. 6 is a flow chart of a method for providing a recommendation using a model, in accordance with a representative embodiment.

FIG. 14 shows an image and various color planes thereof, in accordance with a representative embodiment.

FIG. 15 shows examples of segmentation of images of stool samples for a mucus analysis, in accordance with a representative embodiment.

DETAILED DESCRIPTION

Figure 1:
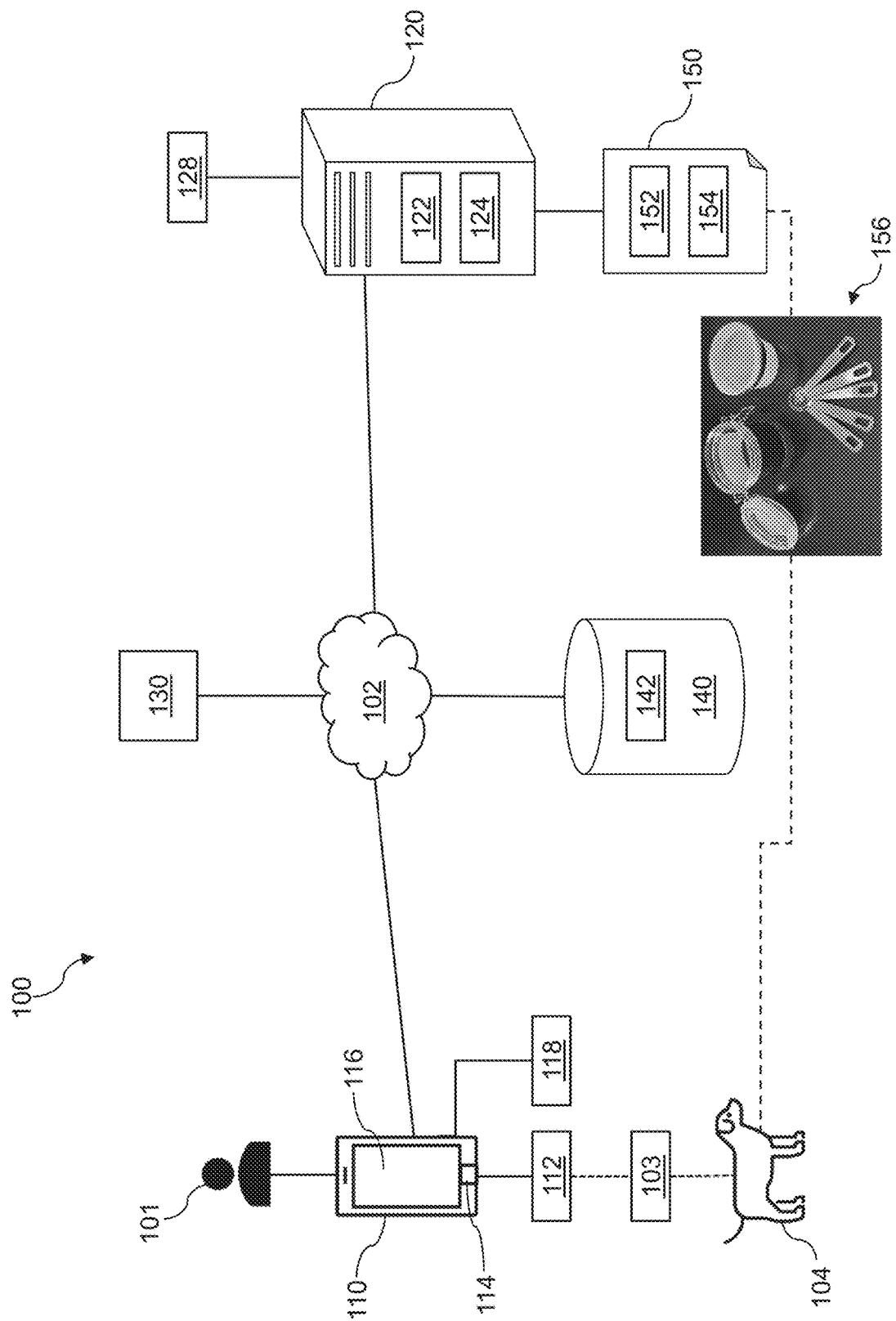
FIG. 1 illustrates a system for animal health assessment, in accordance with a representative embodiment.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "about," "approximately," or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless specifically stated to the contrary.

In general, the devices, systems, and methods disclosed herein generally relate to evaluating animal health, including but not limited to gastrointestinal health. And in particular, this application builds upon the teachings of Int'l Pat. App. No. PCT/US20/44507 filed on Jul. 31, 2020, which is incorporated by reference herein in its entirety, and which included microbiome and/or metabolome assessment, employing specimen image assessment as a complement and/or substitute for microbiome and/or metabolome assessment methods (e.g., traditional microbiome and/or metabolome assessment methods), and personalized health systems (including but not limited to a personalized digestive supplement, cosmetic preparation, dosing method, and package for transporting the health system). However, while Int'l Pat. App. No. PCT/US20/44507 includes teachings obviating existing lab-based assessments of biological specimens such as stool through on-demand image analysis of these biological specimens, the present teachings uncover related, novel applications, including the creation of standard assessment scales and techniques for image-based analysis of certain biological specimens (e.g., mucus and the like) where no laboratory-based assessment exists today, given the transient nature of these specimens. Thus, the present teachings may include the use and analysis of an image of a biological sample including mucus. It will be understood that the present teachings can be used with or instead of the various analyses outlined in Int'l Pat. App. No. PCT/US20/44507. For example, one or more techniques according to the present teachings may be combined with one or more techniques described in Int'l Pat. App. No. PCT/US20/44507 to formulate a relatively comprehensive health assessment for an animal.

However, it will be understood that, although the present teachings may emphasize the use and analysis of an image of mucus (e.g., a biological sample that includes mucus and other material—such as a stool sample that contains mucus thereon or therein—or a biological sample that solely consists of mucus), the techniques discussed herein could also or instead be used to analyze images of other biological material and/or physiological areas. For example, in addition to or instead of an image of mucus, the present teachings may be used for analyzing blood, where "on-demand" aspects of the present teachings may be advantageous as blood can discolor or otherwise change as a function of time. Moreover, in addition to or instead of mucus and blood, the following is a non-exclusive list of biological specimens that can be analyzed using or adapting the present techniques for providing a health assessment based on the analyses: snot, phlegm, plaque, tonsil stones, semen, vaginal discharge, other biological discharge, other portions of an animal's body, combinations thereof, and the like. Thus, the term "biological sample" or "biological specimen" as used herein will be understood to include one or more of the above, and similar.

Further, as used herein, it will be understood that the term "animal" as used herein shall generally refer to any living (or previously living) organism having specialized sense organs and a nervous system, e.g., where the living organism is able to respond to stimuli. Examples of animals include, but are not limited to, companion animals (e.g., dogs, cats, and the like), primates, humans, lizards, and other zoological creatures. For example, an aspect of the present teachings may be used by a pet owner for obtaining a health assessment of their pet based at least in part on an analysis of an image of their pet's stool (or an image of another biological feature or deposit of the pet, e.g., a deposit that contains mucus or the like). In particular, in an aspect of the present teachings, at least a portion of the image analysis, and/or useful information garnered therefrom, can be obtained relatively quickly—e.g., while walking one's dog, a user can take an image of a mucus sample, upload the image to a web-based platform, and obtain at least a partial analysis of the image in near real time.

The term "personalized" and its conjugates as used herein shall generally refer to an outcome that has been customized or tailored specifically to an animal or a user.

The term "questionnaire" as used herein shall generally refer to any solicitation of information from a user (e.g., a caretaker or a patient), which can be recorded electronically, written physically, and so on. A "questionnaire" may also or instead include a solicitation of information from an animal as that term is defined herein. In this manner, by way of example, a "questionnaire" may include a solicitation of data from sources other than an image submitted for analysis—for example, geolocation information, heart rate information or other physiological information (which may be measured via a wearable device or measured manually, e.g., via a stethoscope from a trained health associate), diet or supplement information, activity information, age, sex, weight, stool weight, health condition and history, medications, surgeries, species or breed, and the like. Thus, a "questionnaire" may also or instead include a solicitation of medical information, e.g., from a medical exam. Information derived from such a "questionnaire" may thus include any of the foregoing types of information or similar. It will also be understood that information derived from such a "questionnaire" may be included as "metadata" as that term is used herein and defined below, and a questionnaire itself may also be included as metadata.

The term "metadata" as used herein in the context of the present teachings shall generally refer to any data usable in the present teachings that is different from data generated in an analysis of the content of an image—e.g., any data distinct from data derived directly from the image processing techniques described herein. However, it will be understood that metadata may include information associated with the image that is different from an image analysis of its content—e.g., a date, a time, a file name, a file type, file directory and/or other storage-related information, a file source, a creator of the file, a file size, and the like.

Moreover, as described above, information derived from a questionnaire may be considered metadata. Also or instead, metadata may include data received from a laboratory analysis, e.g., a laboratory analysis of a biological sample from an animal or of the animal itself. In general, such data received from a laboratory analysis will be understood to include data derived using a quantitative tool and/or data that includes a standardized output. It will thus be further be understood that the health assessment techniques included herein may utilize image analysis in combination with metadata such as laboratory-based analyses, including without limitation one or more of a microbiome assessment, a metabolome assessment, bloodwork analysis, urine analysis, a biopsy, parasitology assessment, and so on. In certain embodiments, however, image analysis may be used in lieu of a laboratory-based analysis. Further, in such aspects, the image analysis may be used to make assessments regarding output that is where there is no corresponding laboratory-based analyses, such as an analysis of an animal's mucus or the like. And while a focus of the description may include gastroenterology health, the use of such image analysis as described herein to predict other health, lifestyle, and/or diet characteristics would be recognized by a person of ordinary skill in the art, and therefore does not depart from the spirit and scope of the present teachings.

The term "attribute" as used herein shall generally refer to an image artifact identified by a convolutional neural network or the like (e.g., a color channel, a pixel distance, one or more geometric features, and the like). This may include one or more of a visible aspect or property of content of an image, a measurable aspect or property of content of an image, a calculated aspect or property of content of an image, and/or an aspect or property derived from any of the foregoing or similar. Thus, in general, an "attribute" may include something that is measurable (e.g., a fundamentally measurable entity), observable (such as allowing a human user, and/or a computer program, to grade against a criterion for a specific attribute), calculatable, and/or otherwise derivable through an image analysis. By way of example, specific attributes that can be useful in the context of the present teachings may include one or more of a geometric attribute, a texture attribute, a surface area attribute, an opacity attribute, and/or a color attribute of contents of an image—where these attributes may be calculatable or otherwise discernable from analyzing the image.

The term "feature" as used herein shall generally refer to an input or datapoint used by a model of the present teachings, e.g., where the feature is specially tailored for use by the model. In this manner, a feature can include one or more attributes as described above. However, it will be understood that some attributes may not be usable by a model in their raw, unedited, untranslated, and/or untransformed form, and thus for such attributes to become features, further action may be required such as one or more of editing, reformatting, transforming, and the like. The same may be true for metadata—a feature can include some metadata, and/or metadata can be manipulated or transformed to become a feature to be used as input by a model of the present teachings. In this manner, a feature may include a derivative and/or the wrangling of a raw attribute (e.g., pixel intensity within an image) and/or metadata (e.g., a setting of a camera that captured the image) for use by a model.

The term "characteristic" as described herein may include its standard dictionary definition such as a distinguishing quality of an item (animate or inanimate). As such, a characteristic as used herein may have some overlap with an attribute as described herein and defined above, but while an attribute is generally measured, calculated, and/or otherwise derived from an image, a characteristic as used herein can generally include qualities that can be measured, calculated, and/or otherwise derived (or may otherwise exist or be known) independent from any image or image analysis.

Before detailing the present teachings, some context related to more traditional health assessment techniques may be helpful. For example, current techniques for assessing gastrointestinal health may include a user providing a stool specimen and/or questionnaire responses related to health, behavior, current diet, and other ethnographic information, which are then analyzed and compared to a reference database in order to provide a personalized health plan. An example of this are websites that offer a matching service whereby a user fills out a questionnaire and can take an optional microbiome assessment in order to achieve the best match for a nutrition plan, including a specific dog food offering. Another example is U.S. Pat. No. 9,633,831, which is hereby incorporated by reference herein.

Furthermore, visual assessment may also include a diagnostic assessment such as that described in U.S. Pat. App. Pub. No. 2017/0303901, which is hereby incorporated by reference herein, and which appears to contemplate a feces color detection device provided on a toilet seat. However, such a technique may be rather impractical for high adoption rates.

Moreover, and by way of example, the receipt of an image of a biological sample and application of algorithms to generate a classification is detailed in U.S. Pat. No. 10,043,054, which is incorporated by reference herein in its entirety—however, these teachings are not readily accessible as the specimen preparation requires in-depth laboratory preparation and treatment that is unavailable to the average person.

An example of personalized health systems and products includes U.S. Pat. App. Pub. No. 2017/0148348, which is hereby incorporated by reference herein, and which appears to contemplate a method for generating a personalized supplement recommendation. Moreover, U.S. Pat. App. Pub. No. 2017/0156386, which is hereby incorporated by reference herein, appears to contemplate a system for producing a nutritional composition where the nutritional dispenser is operatively linked to a controller and is configured to produce the personalized nutritional composition. Lastly, U.S. Pat. No. 8,762,167, which is hereby incorporated by reference herein, appears to contemplate a system for deriving a personalized health and fitness plan for an individual. Unfortunately, these health systems may require lengthy and involved analyses that can often take several weeks to months to process, and due to the acute nature of some health conditions, this may be an unacceptable process from a patient engagement and a diagnosis/treatment timeline perspective.

A personalized supplement typically may be derived from laborious, time-intensive methods, which may not be ideal for animals. For example, U.S. Pat. App. Pub. No. 2011/0014351, which is hereby incorporated by reference herein, appears to contemplate a computer-implemented method, apparatus, system, and packaging for providing a daily nutritional supplement component regimen, including a series of daily packets. However, the hurdle of feeding supplements to animals may not be solved by this technique. Regardless of the ability of a computer to create the appropriate formula, the dosing method should be ideal for intake on a consistent basis. Administering pills to an animal may be a significant barrier to compliance.

For mucus-related studies and the like, in laboratory or research practice, it is commonplace to employ mouse, rat, and/or canine models, e.g., as an approximation for human studies. The method of analysis can include sacrificing the animal and performing an autopsy to determine mucus thickness; however, determination of the physical and optical properties thereof is not well documented.

Thus, existing techniques may not substantially address the ability to study fleeting or transient membranes or samples as a part of a digestive health assessments linked to scientific biomarkers as an indicator of health or illness, and a translation of such assessments into a personalized solution that enforces compliance. As such, disclosed herein are systems and methods that can utilize an analysis of an image of a biological sample (e.g., a client-supplied image of gastrointestinal mucus) as a basis for creating a standard mucus assessment scale and using this scale to form a health assessment for an animal related thereto—e.g., in addition to or instead of traditional laboratory analyses and information gathering such as questionnaires and the like.

A high-level workstream of an aspect of the present teachings will now be described for context and by way of example. First, a user uploads a digital image (e.g., photograph) of a biological sample from an animal—e.g., a digital photograph of a mucus sample from their pet that is taken with the user's smartphone and uploaded via a mobile application, electronic mail, and/or a website—to a database management system, which then prepares the image for analysis. Images may thus be acquired from users and retrieved from database management systems and the like. The image may then be passed into an image analysis pipeline, where this pipeline may include analyses operations such as one or more of region of interest extraction, image normalization, feature engineering, and a modeling phase. One or more models may ultimately predict one or more health indices based on one or more features derived from the image.

FIG. 1 illustrates a system for animal health assessment, in accordance with a representative embodiment. More particularly, the system 100 may be used for analyzing an image of a biological sample (e.g., an image containing mucus or the like) to provide a health assessment of an animal. In general, the system 100 may include a networked environment where a data network 102 interconnects a plurality of participating devices and/or users 101 in a communicating relationship. The participating devices may, for example, include any number of user devices 110, remote computing resources 120, and other resources 130. Generally, the system 100 may be used for any of the implementations of the present teachings described herein. For example, the system 100 may be used for analyzing an image 112 of a biological sample 103 to provide a health assessment 150 of an animal 104. More specifically, in the system 100, a user 101 may capture or otherwise retrieve an image 103 of the biological sample 103 related to the animal 104, transmit that image 103 over the data network 102 to a remote computing resource 120 for processing and analysis, where the remote computing resource 120 then provides output of the analysis (e.g., a health assessment 150, which may be in the form of a report or the like) to the user 101 over the data network 102. This entire process can be done relatively quickly, e.g., in near real-time (such as less than five minutes, less than one minute, or mere seconds). Certain participants and aspects of the system 100 will now be described.

The user 101 may be associated with the animal 104 and the user device 110. For example, the animal 104 may include a pet (e.g., a dog, a cat, and the like), and the user 101 may be an owner of the pet, a member of the same household as the pet, or otherwise associated with the pet (e.g., a caretaker, medical personnel, and the like). In some instances, the user 101 themselves may be the animal 104—i.e., where the animal 104 is a human. The user 101 may also or instead include a medical professional (e.g., a doctor, a veterinarian, a nurse, and the like), a researcher, a scientist, a laboratory technician, a student, and so on. In some instances, the user 101 may not be human, but instead the user 101 may include a computing device, computer program, or the like—e.g., where the user 101 is a computer-program product comprising computer executable code embodied in a non-transitory computer readable medium that, when executing on one or more computing devices (e.g., the user device 110)—that is configured to capture, create, edit, receive, and/or transmit an image 112 for processing and analysis as described herein for obtaining a health assessment 150 or the like.

The animal 104 may be any as described herein—i.e., any living (or previously living) organism having specialized sense organs and a nervous system. In certain implementations, the animal 104 is a companion animal such as a dog, a cat, and the like.

The biological sample 103 may be related to the animal 104. For example, in an aspect, the biological sample 103 includes stool that was excreted by the animal 104, where this stool sample also contains mucus or the like, and where analysis of the biological sample 103 includes, at least in part, an analysis of the mucus contained thereon or therein. In this manner, in an aspect where the biological sample 103 includes stool that was excreted by the animal 104, it will be understood that the biological sample 103 may also or instead include other substances deposited by the animal 104 (in addition to, or instead of, stool) such as mucus, a foreign object (e.g., part of a chew toy), blood, a parasite (e.g., a tapeworm and/or its eggs/larvae), hair, microorganisms, microbiomes, metabolomes, and the like. Thus, the biological sample 103 may include stool and one or more other substances in an aspect. In other aspects, the biological sample 103 also or instead includes other biological substances or discharge as described above.

The biological sample 103 may also or instead include a portion of the animal 104 itself. For example, the biological sample 103 may include a physiological area (internal and/or external) of the animal 104. In this manner, the biological sample 103 may include at least a portion of one or more of skin of the animal 104, fur of the animal 104 (and/or hair of the animal 104), a mouth of the animal 104 (e.g., one or more of teeth, gums, plaque, tongue, throat passage, and the like), an ear of the animal 104, an eye of the animal 104, a nose of the animal 104, the throat of the animal 104, an extremity of the animal 104 (e.g., arms, legs, feet, paws, and so on), nails of the animal 104, the anus of the animal 104, sexual and/or reproductive organs of the animal 104, an organ of the animal 104, blood vessels of the animal 104, a muscle of the animal 104, a joint of the animal 104, a tendon of the animal 104, other portions of an animal's body, and so on. Furthermore, the biological sample 103 may also or instead include an abnormality of the animal 104 (e.g., a growth such as a tumor, a rash, an infection, a blemish, and so on), an injury, a mutation, and so on.

The biological sample 103 may also or instead include other secretions, discharges, internal substances, and so on, as described above. For example, the biological sample 103 may include mucus (e.g., alone or in combination with another biological sample 103, such as mucus present in a stool sample), phlegm, snot, urine, vomit, bile, blood, vaginal discharge, semen, other biological discharge, and the like.

Thus, as discussed above, it will be understood that, although the present teachings may emphasize the use and analysis of an image 112 of a biological sample 103 of stool containing mucus or the like, the system 100 may also or instead include other biological samples 103 including other biological material and/or physiological areas.

The data network 102 may be any network(s) or internetwork(s) suitable for communicating data and information among participants in the system 100. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMAX-Advanced (IEEE 802.16m)), fifth generation (e.g., 5G), and/or other technologies, as well as any of a variety of corporate area or local area networks and other switches, routers, hubs, gateways, and the like that might be used to carry data among participants in the system 100.

Each of the participants of the data network 102 may include a suitable network interface comprising, e.g., a network interface card, which term is used broadly herein to include any hardware (along with software, firmware, or the like to control operation of same) suitable for establishing and maintaining wired and/or wireless communications. The network interface card may include without limitation a wired Ethernet network interface card ("NIC"), a wireless 802.11 networking card, a wireless 802.11 USB device, or other hardware for wired or wireless local area networking. The network interface may also or instead include cellular network hardware, wide-area wireless network hardware or any other hardware for centralized, ad hoc, peer-to-peer, or other radio communications that might be used to connect to a network and carry data. In another aspect, the network interface may include a serial or USB port to directly connect to a local computing device such as a desktop computer that, in turn, provides more general network connectivity to the data network 102.

The user devices 110 may include any devices within the system 100 operated by one or more users 101 for practicing the techniques as contemplated herein. The user devices 110 may thus be coupled to the data network 102. Specifically, the user devices 110 may include any device for capturing an image 112 (e.g., a photograph)—or otherwise creating, preparing, editing, or receiving the image 112—and transmitting the image 112 for analysis (e.g., over the data network 102). To this end, the user device 110 may include a camera 114 or the like, or the user device 110 may otherwise be in communication with a camera 114 or the like. In a preferred implementation, the user device 110 includes a smartphone or the like having an internal camera 114, processing capability, and access to the data network 102, all in a one device. The user device 110 may also or instead include any device for receiving output of an analysis of the image 112 over the data network 102, e.g., displaying such output on a graphical user interface 116 thereof. Similarly, the user device 110 may include any device for creating, preparing, editing, receiving, and/or transmitting (e.g., over the data network 102) other data or files in the system 100, such as metadata 118 related to the image 112, the animal 104, the user 101, and so on. The user devices 110 may also or instead include any device for managing, monitoring, or otherwise interacting with tools, platforms, and devices included in the systems and techniques contemplated herein. The user devices 110 may be coupled to the data network 102, e.g., for interaction with one or more other participants in the system 100. It will also be understood that all or part of the functionality of the system 100 described herein may be performed on the user device 110 (or another component of the system 100) without a connection to the data network 102—by way of example, a closed network native application on a smartphone may be utilized, whereby functionality (e.g., one or more of the models 128 described herein) can run in a closed environment.

By way of further example, the user devices 110 may include one or more desktop computers, laptop computers, network computers, tablets, mobile devices, portable digital assistants, messaging devices, cellular phones, smartphones, portable media or entertainment devices, or any other computing devices that can participate in the system 100 as contemplated herein. As discussed above, the user devices 110 may include any form of mobile device, such as any wireless, battery-powered device, that might be used to interact with the networked system 100. It will also be appreciated that one of the user devices 110 may coordinate related functions (e.g., performing processing and/or analysis of the image 112 and the like) as they are performed by another entity such as one of the remote computing resources 120 or other resources 130.

Each user device 110 may generally provide a user interface 116. The user interface 116 may be maintained by a locally-executing application on one of the user devices 110 that receives data from, for example, the remote computing resources 120 or other resources 130. In other embodiments, the user interface 116 may be remotely served and presented on one of the user devices 110, such as where a remote computing resource 120 or other resource 130 includes a web server that provides information through one or more web pages or the like that can be displayed within a web browser or similar client executing on one of the user devices 110. The user interface 116 may in general create a suitable visual presentation for user interaction on a display device of one of the user devices 110, and provide for receiving any suitable form of user input including, e.g., input from a keyboard, mouse, touchpad, touch screen, hand gesture, or other use input device(s).

The remote computing resources 120 may include, or otherwise be in communication with, a processor 122 and a memory 124, where the memory 124 stores code executable by the processor 122 to perform various techniques of the present teachings. More specifically, a remote computing resource 120 may be coupled to the data network 102 and accessible to the user device 110 through the data network 102, where the remote computing resource 120 includes a processor 122 and a memory 124, where the memory 124 stores code executable by the processor 122 to perform the steps of a method according to the present teachings—such as any of the methods or techniques described herein.

The remote computing resources 120 may also or instead include data storage, a network interface, and/or other processing circuitry. In the following description, where the functions or configuration of a remote computing resource 120 are described, this is intended to include corresponding functions or configuration (e.g., by programming) of a processor 122 of the remote computing resource 120, or in communication with the remote computing resource 120. In general, the remote computing resources 120 (or processors 122 thereof or in communication therewith) may perform a variety of processing tasks related to analyzing an image 112 of a biological sample 103 to provide a health assessment of an animal 104 related to the biological sample 103 as discussed herein. For example, the remote computing resources 120 may manage information received from one or more of the user devices 110 (e.g., the image 112, metadata 118, and so on), and provide related supporting functions such as parsing or segmentation of the image 112 for analysis, normalization of the image 112, performing calculations, identifying and extracting various properties and attributes of the image 112, calculating features of the contents of the image 112, applying one or more models 128 and/or algorithms to the image 112 and/or metadata 118, retrieving and/or analyzing information from a database 140 and/or the memory 124, providing a health assessment 150, communicating with other resources 130 and the participants in the system 100, storing data, and the like. The remote computing resources 120 may also or instead include backend algorithms that react to actions performed by a user 101 at one or more of the user devices 110. These backend algorithms may also or instead be located elsewhere in the system 100.

The remote computing resources 120 may also or instead include a web server or similar front end that facilitates web-based access by the user devices 110 to the capabilities of the remote computing resource 120 or other components of the system 100. A remote computing resource 120 may also or instead communicate with other resources 130 in order to obtain information for providing to a user 101 through a user interface 116 on the user device 110. Where the user 101 specifies certain criteria for analysis or otherwise, this information may be used by a remote computing resource 120 (and any associated algorithms) to access other resources 130. Additional processing may be usefully performed in this context such as recommending certain analyses and processing operations and techniques.

A remote computing resource 120 may also or instead maintain, or otherwise be in communication with, a database 140 of data 142, and optionally with an interface for users 101 at the user devices 110 to utilize the data 142 of such a database 140. Thus, in one aspect, a remote computing resource 120 may include a database 140 of data 142, and the remote computing resource 120 may act as a server that provides a platform for selecting and using such data 142, and/or providing supporting services related thereto. The database 140 may be a local database of the remote computing resource 120, or a remote database to the remote computing resource 120 or another participant in the system 100. Thus, the database 140 may include a cloud-based database or the like.

A remote computing resource 120 may also or instead be configured to manage access to certain content (e.g., for a particular user 101). In one aspect, a remote computing resource 120 may manage access to a component of the system 100 by a user device 110 according to input from a user 101.

Thus, and as described throughout the present disclosure, a remote computing resource 120 coupled to the data network 102 and accessible to the user device 110 through the data network 102 may include a processor 122 and a memory 124, where the memory 124 stores code executable by the processor 122 to perform the steps of: receiving an image 112 from the user 101 over the data network 102, the image 112 including a biological sample 103 containing mucus (e.g., mucus accompanying stool); identifying and extracting one or more regions of interest within the image 112 for further analysis; applying a model 128 to the regions of interest to identify one or more conditions of mucus therein, the model 128 trained using a plurality of images having varying conditions of mucus, where output of the model 128 includes at least a grade corresponding to an amount of mucus present in the one or more regions of interest; based at least in part on the output of the model 128, predicting a health characteristic 152 of an animal 104 from which the biological sample 103 originated; and presenting the health characteristic 152 to a user 101 associated with the animal 104 (e.g., presenting the health characteristic 152 or information related thereto on the user device 110). The code may further perform the step of transmitting a treatment 154 to the user device 110 over the data network 102 in view of the health characteristic 152, e.g., in a report or another form of a health assessment 150.

The data 142 stored in a database 140 of the system 100 may include reference information for use by the remote computing resource 120 for providing the health assessment

150. For example, this data 142 may include historical data such as information from analyses of one or more biological samples 103 (e.g., from the same animal 104 or a different animal). The data 142 may also or instead include one or more models 128, e.g., for retrieval and use by the remote computing resource 120 or another participant for processing and analyzing the image 112 or other information to generate the health assessment 150. The data 142 may also or instead include a plurality of images 112 (e.g., of the same or different biological sample 103, from the same animal 104 or a different animal, and so on). The data 142 may also or instead include a number of correlations and/or associations between one or more image-based features of a biological sample 103 and one or more of a microbiome presence and/or characteristic, a metabolome presence and/or characteristic, a health characteristic, a diet characteristic, and the like.

As discussed herein, the systems 100 and techniques of the present teachings may include and utilize one or more models 128 that are configured and programmed to perform certain tasks to assist with the various analyses described herein. By way of example, parsing the image 112 that is received or retrieved for analysis may involve segmenting the image 112, which can be performed at least in part by a specific segmentation model, e.g., a deep learning model. This segmentation model may read-in the image 112 and label specific classes in the image 112 (e.g., a class for the biological sample 103 and a class for background), where the segmentation model can be rewarded for correctly identifying certain pixels and punished when the segmentation model is incorrect when identifying certain pixels. The segmentation model may thus be configured to extract the background from the image 112 for analysis of only the biological sample 103 contained within the image 112. The segmentation model may also or instead normalize one or more attributes of the content within the image 112, normalize one or more color planes of the content within the image 112, account for lighting or other conditions, and so on. By way of example in the context of a biological sample 103 including mucus contained within a stool sample, a segmentation model may define a region of interest within an image 112, which may be a region of the stool sample wholly or partially containing mucus, for extraction/analysis of a visual feature thereof (e.g., after a normalization is performed).

A model 128 can also or instead include a geometric model—e.g., a model 128 specifically configured and programmed to identify and determine (e.g., calculate) geometric features of content within the image 112—e.g., geometric features including but not limited to morphological region properties, which can include one or more of contiguous pixel areas, a perimeter, major/minor axes, and the like. Such a geometric model may include machine-learning models such as random forest. These models can optionally be trained with optimized hyper parameters using a grid search routine, which may have advantageous accuracy. Such a geometric model may also or instead include other machine learning models, including without limitation, one or more of k-nearest neighbor, support vector machine, logistic regression, decision trees (which can be gradient-boosted and/or combined in ensemble architectures), Naïve Bayes, Multi-Layer Perceptron, or the like.

A model 128 can also or instead include a color model—e.g., a model 128 specifically configured and programmed to identify and determine color of contents within the image 112, or other color-related attributes and/or features. Such a color model may include a multilinear model, e.g., with lasso correction or the like. The output of color model may include a color index, which can be in the form of a color wheel, a list of colors within a portion of the image 112, a sum of the top color planes, and the like. The output of color model may also or instead include a prediction for a Bristol stool score or the like (when the biological sample 103 is a stool sample), which can be used as a health characteristic 152 for formulating a treatment 154 and/or a health assessment 150. The output of color model may also or instead include a mucus health score or the like, which can be indicative of a health prediction based on a color or other condition of mucus contained within the biological sample 103.

As used herein, a "mucus health score" or the like may include one or more of a grade, label, rating, and the like, or any other information related to the health of an animal based at least in part on an analysis of its mucus, e.g., from an analysis of an image of a biological sample of the animal that contains mucus (or that completely lacks mucus). In general, such a mucus health score may represent a holistic assessment of one or more mucus characteristics that are identified and/or derived from an image analysis of a biological sample, where one of more of these characteristics may include an amount of mucus present (or absence of mucus), an opacity, a thickness, a surface area occupied by mucus, a color, an estimate of microbial content, an estimate of a level of cortisol in the host animal, an estimate of a level of bacteria, detection of blood, detection of a pathogen, a texture, a viscosity, a consistency, a volume, a mass, and the like. The mucus health score may thus include a combination and/or scaling of other scores such as a grade corresponding to an amount of mucus present, a color score, an opacity score, a texture score, a viscosity score, a consistency score, a mass score, and so on.

A model 128 may also or instead include a convolutional neural network—e.g., a model 128 specifically configured and programmed to determine a mucus coating level within an image 112, and/or other mucus-related attributes and features. Such a model 128 may be a ResNet-18 convolutional neural network, although ResNet-34 could also or instead be employed. Other networks such as VGG could also or instead be employed. The output of this model 128 may include a mucus index, which can be in the form of a grade, scale, label, and/or metric. The output of the model 128 may also or instead include a prediction for a health score or the like, which can be used as a health characteristic 152 for formulating a treatment 154 and/or a health assessment 150.

Also, or instead, k-mean image segmentation may be utilized in the present teachings, where a pseudo-color plane is created (e.g., specifically for the present teachings), which can allow the present teachings to identify and determine the top 'n' most abundant colors in an image. This can also or instead permit the present teachings to identify and determine color homogeneity within an image.

Supervised machine learning may find an association between data (e.g., feature vectors X) and a corresponding label (y, which can be categorical or continuous) so that the computer can learn an algorithm, f, that maps the input to the output (e.g., y=f(X)). Two further subgroups can include classification and regression problems, where the supervised machine-learning model is trained to predict categorical data (e.g., predicting a mucus health score from an image) and continuous data, respectively (e.g., predicting a mass from an image). Some examples of models include: support vector machines, stochastic gradient descent, k nearest neighbors, decision trees, neural networks, and so on, where a longer list can be found here by way of example: https://scikit-learn.org/stable/supervised_learning.html#supervised-learning.

Unsupervised machine learning may assume a similar structure to supervised machine learning, except that no training labels y may be used. These models may attempt to learn the underlying structure or distribution of the data to learn more about its behavior. Some example of tasks here are clustering (e.g., principal component analysis (PCA) for microbiome work) and associations (e.g., Apriori algorithms for association rule learning). A longer list can be found here by way of example: https://scikit-learn.org/stable/unsupervised_learning.html.

Semi-supervised approaches may occur when practitioners feed in a partial list of labeled training data. This typically increases accuracy as a result of using labeled data, but allows for practitioners to minimize cost (e.g., time and monetary to gather labeled data). A longer list can be found here by way of example: https://scikit-learn.org/stable/modules/label_propagation.html.

Transfer learning may include a technique that leverages open-source models that have been trained on significantly more images. For example, Inception was trained on 1.4M images, and is a well-known network for classification tasks. The model and/or model weights can be adapted for a custom task by appending a custom deep neural network after an appropriate layer in Inception to tune the model weights towards a custom classification task according to the present teachings.

A model for mucus detection may use transfer learning. To this end, Imagenet pre-trained weights may be retained up to a specific layer in the network, which have increasingly more sensitivity towards their originally designed classification task. A deep neural network may then be appended to previous layers in ResNet, adding hidden layers (e.g., with 256 neurons), creating a dropout pruning to prevent overfitting (e.g., with 40% drop out of the neurons as a regularization step), flattening the resulting network, and a final 3 class classification. In this manner, models may be trained (with ~100s of images) using a pre-trained model (using 1.4M images) and fine tuning last layers to achieve ~75% accuracy.

In general, models 128 may include one or more of a computer vision model (e.g., where such a computer vision model uses semantic segmentation to detect a region of interest within the image 112), a U-Net segmentation model, a machine-learning model (e.g., to predict health of the animal 104 by features of the biological sample 103), a transfer learning model (e.g., where weights are adapted from a network trained in an existing model, such as a VGG-16 model—i.e., trained on classifying ten million images), a correlation model, a deep learning model, and so on.

The other resources 130 may include any resources that can be usefully employed in the devices, systems, and methods as described herein. For example, these other resources 130 may include without limitation other data networks, human actors (e.g., programmers, researchers, annotators, editors, analysts, and so forth), sensors (e.g., audio or visual sensors), data mining tools, computational tools, data monitoring tools, algorithms, and so forth. The other resources 130 may also or instead include any other software or hardware resources that may be usefully employed in the networked applications as contemplated herein. For example, the other resources 130 may include payment processing servers or platforms used to authorize payment for access, content, or option/feature purchases, or otherwise. In another aspect, the other resources 130 may include certificate servers or other security resources for third-party verification of identity, encryption or decryption of data, and so forth. In another aspect, the other resources 130 may include a desktop computer or the like co-located (e.g., on the same local area network with, or directly coupled to through a serial or USB cable) with one of the user devices 110 or remote computing resources 120. In this case, the other resource 110 may provide supplemental functions for the user device 110 and/or remote computing resource 120. Other resources 130 may also or instead include supplemental resources such as cameras, scanners, printers, input devices, and so forth.

The other resources 130 may also or instead include one or more web servers that provide web-based access to and from any of the other participants in the system 100. While depicted as a separate network entity, it will be readily appreciated that the other resources 130 (e.g., a web server) may also or instead be logically and/or physically associated with one of the other devices described herein, and may, for example, include or provide a user interface for web access to a remote computing resource 120 or a database 140 in a manner that permits user interaction through the data network 102, e.g., from a user device 110.

It will be understood that the participants in the system 100 may include any hardware or software to perform various functions as described herein. For example, one or more of the user device 110 and the other resources 130 may include a memory 124 and a processor 122.

The various components of the networked system 100 described above may be arranged and configured to support the techniques, processes, and methods described herein in a variety of ways. For example, in one aspect, a user device 110 connects through the data network 102 to a server (e.g., that is part of one or more of the remote computing resource 120 or other resources 130) that performs a variety of processing tasks related to analyzing an image 112 to provide a health assessment 150 of an animal 104 associated with a biological sample 103 present in the image 112. For example, the remote computing resource 120 may include a server that hosts a website (and/or a mobile application or application programming interface) that runs a platform for analyzing and/or processing an image 112 and other data. More specifically, a user 101 associated with the user device 110 and having appropriate permissions for using the system 100 may use the user device 110 to transmit an image 112 and/or metadata 118 over the data network 102 to the remote computing resource 120. The remote computing resource 120 may receive the image 112 from the user 101 over the data network 102 for processing and analysis thereof, where an output of the processing and analysis may include a health assessment 150.

The health assessment 150 may include a prediction regarding a health characteristic 152 of the animal 104. Such a health characteristic 152 may include one or more of information related to whether the animal 104 is likely sick or healthy, a dietary insight, and so on. For example, a health characteristic 152 may be based on a mucus grade (which may be based on an amount of mucus present in a biological sample 103, or another attribute of mucus contained in a biological sample 103), and accordingly, the health characteristic 152 may be related to a level of digestive stress. By way example, the presence of a relatively large amount of mucus in a stool sample (e.g., yielding a mucus grade of "high") may be an indication of high level of digestive distress in the animal 104 that deposited the stool sample, and the health characteristic 152 and/or health assessment 150 may reflect this predicted condition. The health assessment 150 may also or instead include a treatment 154 prescription and/or recommendation for the animal 104. Such a treatment 154 recommendation may include one or more of a customized health plan, a food, a supplement (e.g., a personalized dietary supplement), a medicine, and so on. The health assessment 150 may be presented or transmitted to the user 101 in the form of a report or the like. It will be understood that, in general and unless stated otherwise, the "report" as described herein may include any share-out of a result of one or more of the analyses performed in the present teachings.

By way of example, as part of the health assessment 150 and/or treatment 154, techniques may involve the creation of a personalized product 156 for the animal 104, and thus the system 100 may include a personalized product 156 and/or related components such as packaging, containers, dosing instruments, and so on. The personalized product 156 may include one or more ingredients derived from a computer-based analysis of one or more features of a biological sample 103 extracted from a model 128 applied to an image 112 that includes the biological sample 103. As described herein, the biological sample 103 may include stool, and, in such instances (and/or in other instances when the biological sample is not stool) the personalized product 156 may include a personalized dietary product. In this manner, one or more ingredients of the personalized product 156 may include a predetermined amount of one or more of a probiotic, a prebiotic, a digestive enzyme, an anti-inflammatory, a natural extract, a vitamin, a mineral, an amino acid, a short-chain fatty acid, an oil, a formulating agent, and the like. The personalized product 156 may also or instead include any as otherwise described herein.

In an aspect, many of the techniques of the present teachings are performed by the remote computing resource 120. For example, the remote computing resource 120 may include an analysis engine (or otherwise a processor 122) configured by computer-executable code to analyze the image 112 and metadata 118, a recommendation engine (or otherwise a processor 122) configured by computer-executable code to provide a recommendation for the animal 104, and so on. However, it will be understood that some of the features and functionality described with reference to the remote computing resource 120 may also or instead be performed by another participant in the system 100.

Figure 2:
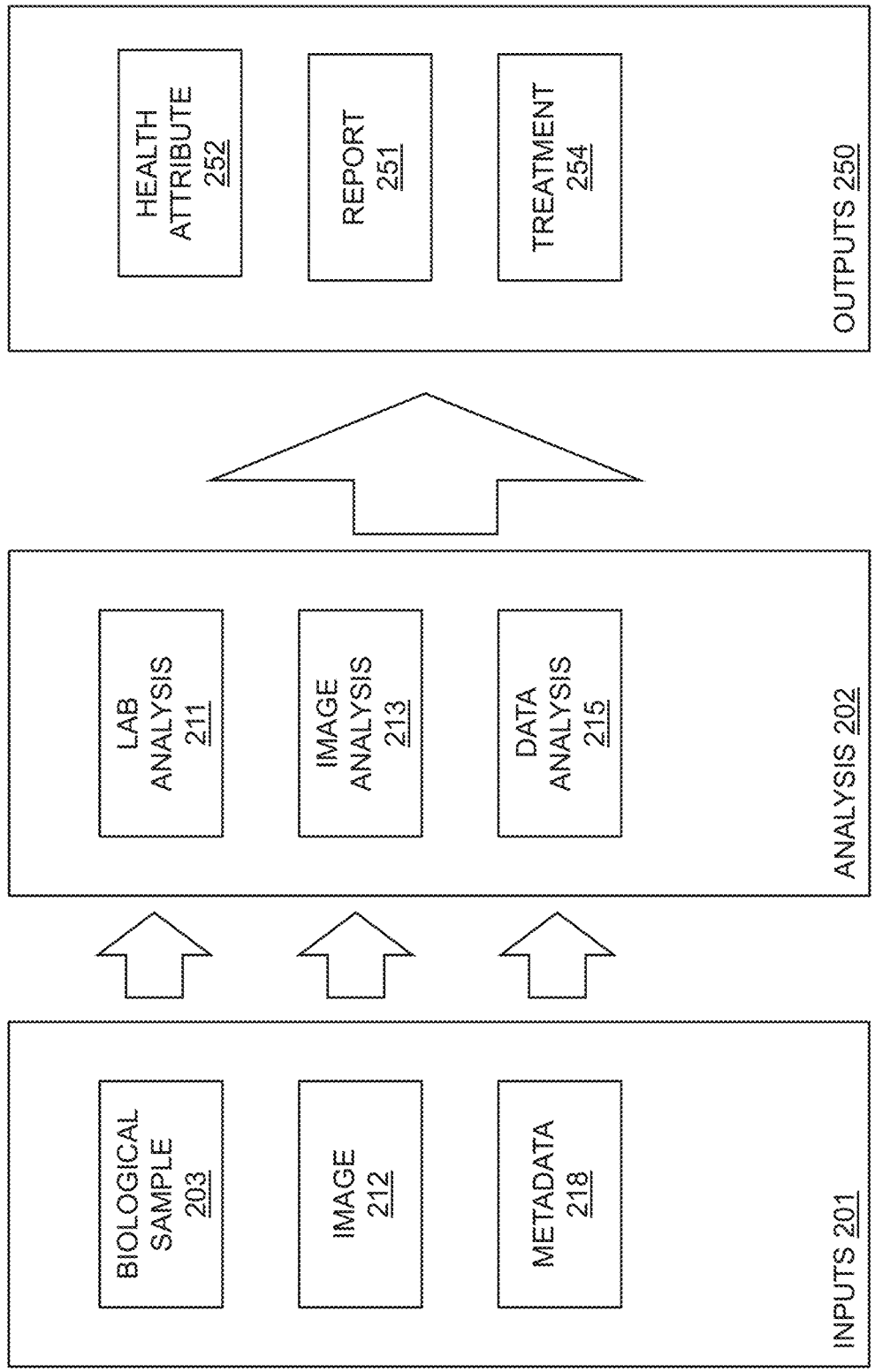
FIG. 2 is a flow diagram illustrating a technique for generating a customized health plan for an animal based at least in part on image analysis of a biological sample, in accordance with a representative embodiment.

FIG. 2 is a flow diagram illustrating a technique for generating a customized health plan for an animal based at least in part on image analysis of a biological sample, in accordance with a representative embodiment. As shown in the figure, inputs 201 may include, but are not limited to, a biological sample 203 from an animal, an image 212 of the biological sample 203, and metadata 218. By way of example, these inputs 201 can include a biological sample 203 in the form of a stool sample containing mucus, an image 212 of the biological sample 203 in the form of a digital file, and metadata 218 in the form of laboratory data and/or questionnaire responses, which may be related to health, behavior, current diet, other ethnographic information, and the like.

The respective inputs 201 may then be analyzed as shown in the analysis 202 portion of the figure. The analysis 202 may include a laboratory analysis 211 (e.g., metabolome and/or microbiome analysis, which may include the extraction, amplification, sequencing, and subsequent analyses thereof), an image analysis 213 of the supplied image 212, and/or a data analysis 202 of the metadata 218 and the like. For one or more of the inputs 201, analyzed data may be compared to a reference database.

The outputs 250 may include, but are not limited to, a prediction regarding a health characteristic 252 of the animal, a report 251 where results are shared with an end user, and a treatment 254. For example, one or more of the health characteristic 252 and the report 251 may be used to create a treatment 254 such as a customized health plan, which may include but is not limited to including a recommendation of personalized dietary supplements along with recommendations for other facets of health such as diet, sleep, exercise, activity, and other lifestyle recommendations for the animal. Thus, the outputs 250 may include shared results of analyses/assessments and personalized solutions for the animal that are created from such results.

It will be understood that the technique shown with respect to FIG. 2 may or may not include the step of providing the actual biological sample 203 for a laboratory analysis 211. Thus, the inputs 201 may solely include the image 212 and metadata 218 for image analysis 213 and data analysis 215.

Figure 3:
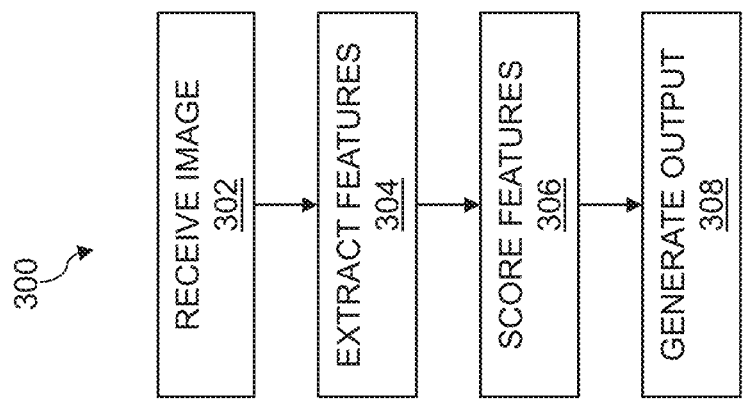
FIG. 3 is a flow chart of a method for assessing animal health based at least in part on image analysis of a biological sample, in accordance with a representative embodiment.

FIG. 3 is a flow chart of a method for assessing animal health based at least in part on image analysis of a biological sample, in accordance with a representative embodiment. As shown in step 302, the method 300 may include receiving an image of a biological sample, e.g., a raw image of mucus or the like (e.g., present on another biological sample, such as stool) in the form of a digital photo file. In this method 300, an image of a biological sample may be analyzed among a collection of predetermined factors, including but not limited to color, opacity, texture, viscosity, consistency, surface area (of a specimen itself, or coverage of a substance along a particular surface area of a specimen), volume, mass, and the like. The biological sample may be collected in a controlled manner, e.g., such that visual reference standards are available in the image itself. For example, where the biological sample is a stool sample, this may be achieved by using a stool sample collection bag with a known color, shape, and/or other markings such as text.

As shown in step 304, the method 300 may include extracting features of the biological sample included in the image, and as shown in step 306, the method 300 may include scoring and/or indexing these features. In certain aspects, based on the raw image comparison to a reference database, a score or index may be assigned for each feature that is extracted. Each score, in isolation and/or aggregate, may provide salient data correlated to the presence or absence of specific symptoms or physiological conditions, which can serve as input into a personalization algorithm, with findings provided in a report. Thus, as shown in step 308, the method 300 may include generating output such as a report. Such a report may include or be used to create a personalized health plan, including but not limited to a recommendation of personalized dietary supplements along with other facets of health including diet, sleep, exercise, activity, and other lifestyle recommendations.

The features that may be extracted in the method 300 may include, but are not limited to, one or more of color, opacity, texture, viscosity, consistency, volume, mass, surface area (e.g., the surface area of a substance or covered by a substance), and the like. To this end, the scores that may be assigned can be as holistic as an overall mucus score, and/or can include one or more of a color score, an opacity score, a texture score, a viscosity score, a consistency score, a mass score, and so on. However, it will be understood that examples of features that are extracted from an image as disclosed herein may be provided herein by way of convenience and simplicity. A Convolutional Neural Network (CNN) used in the present teachings for the mucus model provides a good example where, in the CNN, features are extracted based on the filtering operations, which may include features consistent with the definition provided herein, but that may not have any physical interpretation.

Figure 4:
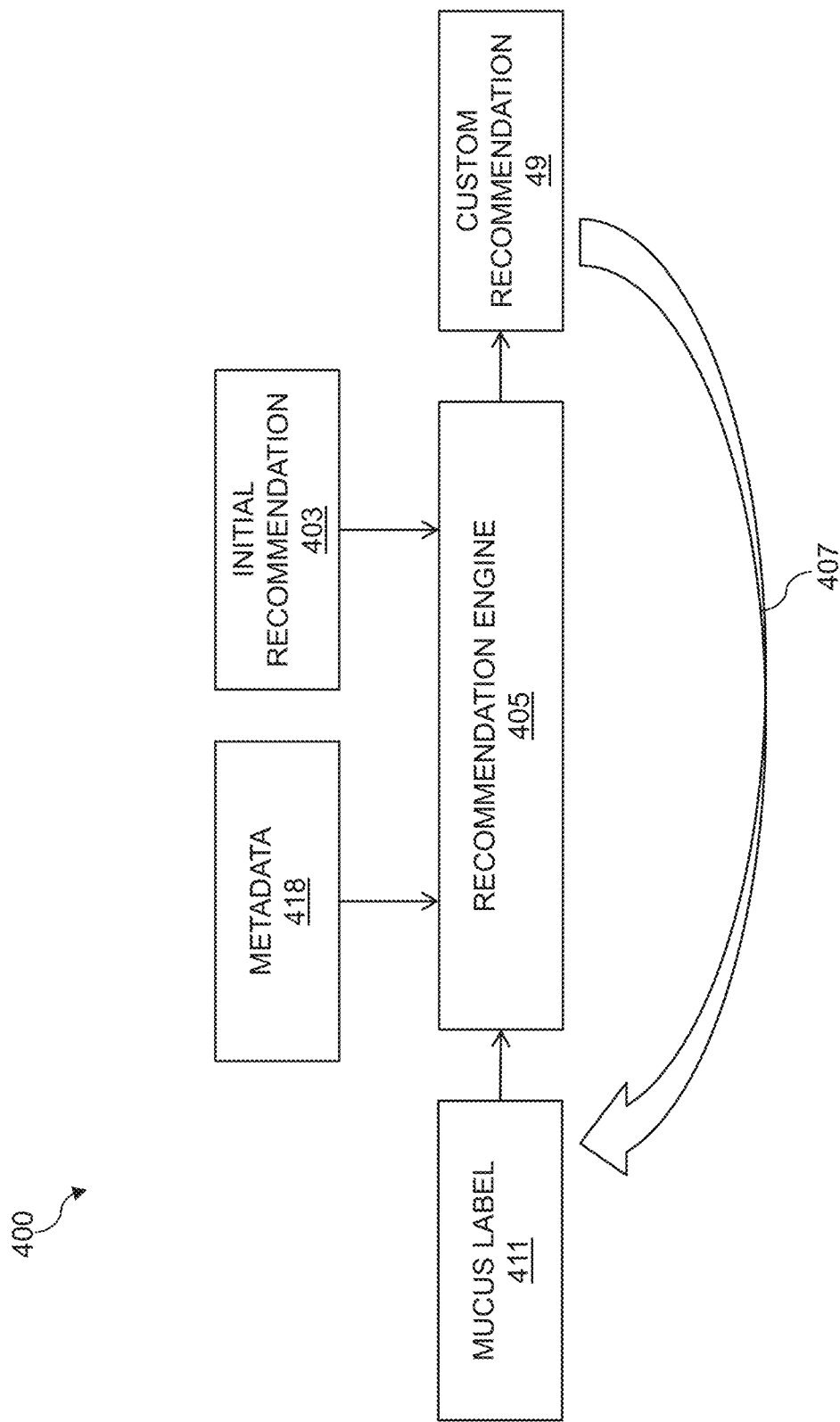
FIG. 4 is a flow diagram illustrating a dynamic recommendation engine with a feedback loop, in accordance with a representative embodiment.

FIG. 4 is a flow diagram illustrating a dynamic recommendation engine with a feedback loop, in accordance with a representative embodiment. More specifically, FIG. 4 shows a system 400 illustrating a dynamic recommendation engine 405 with a feedback loop 407 for further refinement, which may be generated to ensure that a personalized/customized recommendation 409 is assigned to a specific mucus label 411. In other words, once the mucus labels 411 are identified, the system 400 illustrates a recommendation engine 405 that can, with training, operate without any need for laboratory data as input, and merely an image as input. In some instances, the mucus label 411 may wholly consist of, or may otherwise include as part of the label, an overall mucus grade that may, at least in part, be based on an amount of mucus present on a biological sample or region of interest thereof. The mucus label 411 may also or instead include or otherwise correspond to an opacity of mucus present in one or more regions of interest, a thickness of mucus present in one or more regions of interest, a surface area occupied by mucus in one or more regions of interest, a color of mucus present in one or more regions of interest, an estimate of microbial content of mucus present in one or more regions of interest, an estimate of a level of cortisol in the host animal, an estimate of a level of bacteria, detection of blood, detection of a pathogen, combinations thereof, and the like.

The recommendation engine 405 may be formed by taking metadata 418 such as symptomatic data or the like (e.g., from questionnaires), and an initial recommendation 403 (e.g., a hypothesis based at least in part on the metadata 418) to deliver a custom recommendation 409 for an animal. The recommendation engine 405 may be dynamically updated and optimized as more data is added—including but not limited to longitudinal data—to optimize the correspondence between the mucus label 411 and a custom recommendation 409 for an animal.

FIG. 5 is a flow chart of a method for training a model, in accordance with a representative embodiment, and may represent a convolutional neural network (CNN) working process. Specifically, the model trained in FIG. 5 may be one or more of an association model (e.g., a machine-learning model that learns associations between one or more image-based features identified from an analysis of an image of a biological sample and one or more health characteristics for forming a health assessment and/or treatment plan), a correlation model (e.g., a model that correlates one or more image-based features identified from an analysis of an image of a biological sample with a biological label or characteristic, such as a characteristic of mucus present and/or a likely presence or absence of particular substance or micro-organism(s)—it will be understood that a Pearson correlation coefficient may be used to this end), and/or a deep learning model (e.g., a model such as a convolutional neural network (CNN) that can receive and process an input image, calculate and/or assign learnable weights and biases, and be able to form classifications based on those weights and biases). Thus, the method 500 may generally be used for developing new feature models, and, more specifically, the method 500 may include a technique for identifying new features that can be used for machine-learning models to predict health characteristics. That is, the method 500 may involve the use of new computer-vision-based features that can connect images to a likely biological characteristic, such as the presence or absence of mucus and/or a particular microorganism. It will be understood that, in some aspects, these are not correlation models, but rather feature vectors to be used in future machine-learning model development.

By way of example, the method 500 may involve capturing associations to identify what features a system can have resolution towards and these features can be used to build a machine-learning model—e.g., features such as an amount of mucus present, which can be based on a percentage of coverage in a biological sample, which can represent a geometric region property that may show an association with the amount of digestive distress as measured by one or more of host organism cortisol levels, leucocyte levels, pathogenic presence (e.g., parasitic and/or bacterial infection), and/or a dysbiosis of a host animal's microbiome, which can be measured by mean concentrations of pathogenic bacteria or total bacteria within the mucus.

The method 500 may include a technique for training a model such as a CNN that can receive and process an input image, including assigning learnable weights, biases, and the like therefrom. In general this can involve using a baseline, pre-trained model—e.g., a model that has been trained using over one million images—and adapting or further training this model using other, predetermined images in which certain features of interest are known. This may produce a more fine-tuned model that can identify these features of interest in a new image provided for analysis. In certain aspects, in this manner, a CNN model can be trained to detect an amount of mucus present in an image of a biological sample, as well as to detect other features of that mucus such as thickness, surface area, opacity, color, and the like. That is, the model can be trained using hundreds or thousands of images that have been pre-categorized and/or prelabeled with characteristics of mucus, such that a refined model after training can identify and label the aforementioned characteristics of mucus in an image.

The method 500 may also or instead include a technique for training a model that correlates a feature extracted from an analysis of an image of a biological sample containing mucus with the likely presence or absence of a particular metabolome. It will be understood that other correlations and/or associations between features extracted from an image and particular health and/or biological characteristics exist, and that the techniques described herein shall include the training and use of models based on these correlations and/or associations.

As shown in step 502, the method 500 may include acquiring an image of a biological sample, which, for the sake of example, may include a digital photograph of a stool sample that contains mucus therein or thereon. This step 502 may thus include specifically tailoring received images such that the method 500 includes the use of a substantially consistent procedure in processing images. To this end, received images may be processed such that they are in a specific format with specific characteristics after receipt, and/or the capture of an image (e.g., via a user's digital camera on a web-enabled device) may be controlled in a manner that enables substantially consistent processing of such images. Controlling the capture of an image may include adjusting settings for capture and/or providing a means for substantially consistent image capture, such as by applying a background for a biological sample that includes one or more of predetermined markings, colors, shapes, text, and the like.

As shown in step 504, the method 500 may include acquiring image data. Such image data may include metadata accompanying the image (or otherwise received from a user or the like). Such image data may also or instead be extracted from the image itself. In certain implementations, the image data may include ground truths and/or predetermined labels that can be used to train a model as described herein.

As shown in step 506, the method 500 may include processing the image. Processing the image may include resizing or otherwise reformatting the image so that the image is sufficient for analysis by a certain model, e.g., a model to be trained or a fully-trained model. In the training context, processing the image may also or instead include creating labels for image-based features of the biological sample (e.g., stool containing mucus) such as an amount of a substance present (e.g., mucus), a color, an opacity, a texture, an apparent viscosity, an approximate volume and/or mass, a consistency, a surface area, and so on. By way of example, processing an image for training may include assigning a label or grade corresponding to an amount of mucus present in a biological sample, and by way of further example, the label or grade may identify the amount of mucus as one of 'absent,' 'low,' or 'high.'

Processing the image may also or instead include a signal/image processing analysis or the like to identify and/or generate image-based features of the biological sample (e.g., stool containing mucus) such as color, opacity, texture, apparent viscosity, approximate volume and/or mass, consistency, surface area, and so on. Thus, in this manner and generally in a machine-learning context, the method 500 may include extracting features of the image. Signal/image processing may also or instead include linear filtering with labeling. To this end, a filter bank or the like may be utilized, where the filter bank is a set of filters (e.g., Gabor filters tuned at various frequencies and phases) and can be located locally in an analysis engine or the like, and/or may be retrieved for use from a remote resource.

As shown in step 508, the method 500 may include obtaining and applying a model to the processed image. The model may be the pretrained model, where this step 508 involves fine-tuning this model by applying it to a processed image with a known output. For example, the model may be a pretrained, ResNet model. As described above, the known output may be a label or grade corresponding to an amount of mucus present in an image of a biological sample, and/or labels related to other characteristics of mucus contained therein.

As shown in step 510, the method 500 may include receiving data. This data may include output of the model, such as a label or grade for one or more characteristics of mucus or another substance contained in the image. In certain aspects, the output includes a mucus health score or the like. The output of the model may be used to train the model as explained below in step 512.

Receiving data may also or instead include receiving metadata as described herein and/or one or more of ground-truth data, laboratory data, and so on. Using this data and data such as feature extractions from image processing or other output from a model, correlations and/or associations may be uncovered, and/or a model may be trained as explained herein. Thus, in certain aspects, the method 500 may include identifying correlations and/or associations. Also or instead, in certain aspects, further processing of these or other parameters could employ a deep learning network—potentially a Convolutional Neural Network (CNN)—as a model to create a mucus model that learns to associate a mucus label with an input image. Other processing can include dimensionality reduction for clustering (e.g., PCA, Non-Negative Matrix Factorization (NMF), and the like), which can be further used to analyze correlations and/or associations with image features. In this manner, the method 500 can involve associating a microbiome/metabolome characteristic with an image artifact to create a new feature.

As shown in step 512, the method 500 may include training the model. This may include the application of a processed image with a known output, and may involve adjusting the model based on the output received in step 510. For example, training the model may include comparing output of the untrained or partially trained model to one or more of ground truths, predetermined labels, and other known outputs. That is, when the output diverges from a known or expected output, the model may be adjusted so that the output is more likely to coincide with a known or expected output.

As shown in step 514, the method 500 may include testing the model. Testing the model may include, after an adjustment to the model is made, applying the model to an image (e.g., a different image used to train the model, or the same image) and analyzing its output against a known or expected output.

It will further be understood that, in certain aspects, a feature extracted by the model and/or a label/grade as output of a model can be defined by the association between the appearance of a biological sample (e.g., stool containing mucus) and the presence or absence of biological content or substances (e.g., microbiome characteristics and/or metabolome characteristics). And, as described above, other features, labels, grades, and other output of a model may also or instead be defined by the appearance of a biological sample as processed in an image, besides or in addition to the presence or absence of biological substances, such as a health characteristic, a mucus health score, and the like. One example is that a relatively large amount of mucus in stool can typically be attributed to digestive distress, and thus the amount of mucus present can be attributed to a level of digestive distress. Another example is that texture attributes of stool can be attributed a level of hydration of an animal that deposited the stool. Further, because more granular output from advanced image processing can yield more granular health characteristics, the present techniques can include the development of such output and models.

FIG. 6 is a flow chart of a method for providing a recommendation using a model, in accordance with a representative embodiment. The method 600 may be similar to that shown and described above with reference to FIG. 5, but where the model is employed for making a prediction (and subsequently a customized, personalized recommendation for an animal based on a correlation and/or association) without receipt of a laboratory analysis of a physical biological sample from the animal. Thus, as shown in step 602, the method 600 may include acquiring an image of a biological sample (e.g., stool containing mucus); as shown in step 604, the method 600 may include acquiring image data; and, as shown in step 606, the method 600 may include processing the image. Moreover, although when the method 600 is implemented using a CNN or the like this may not be necessary, in certain implementations, the method 600 may include extracting one or more attributes and/or features from the image. And, as shown in step 608, the method 600 may include applying a trained model that can identify a relationship between an image feature and another characteristic.

As shown in step 610, the method 600 may include determining a health characteristic based on the correlation and/or association. For example, this can include determining a mucus label (and/or a biome label, a metabolome label, or another label) based on a correlation and/or association to the extracted image feature. And, as shown in step 612, the method 600 may include providing a recommendation based on the determined health characteristic—e.g., a personalized recommendation for the animal.

The method 600 may also or instead include a testing task, e.g., where some data is held back from the model for testing the model. Images may be acquired and processed in a similar manner as for the training task in FIG. 5, only that the model may already be trained and can now be employed for estimating the learned correlation/association, and further employed by the recommendation engine to generate a personalized recommendation.

Surprisingly, the image analysis algorithm output can be associated or otherwise connected to other input data. This non-obvious result may benefit the method of obviating the biological specimen as a viable alternate means of delivering a personalized health insight, which can be embodied in a personalized health report in a relatively fast manner. Thus, a non-obvious, advantageous result of the present teachings may involve a connection between image attributes/features to health characteristics—which can be accomplished with high-accuracy and substantially faster than a traditional laboratory analysis. For example, a traditional analysis of a stool sample may involve requesting a specimen kit and receiving the same (which can take about 5 days), collecting the stool sample (which can be burdensome, prone to contamination, and unsanitary depending on the collection technique), mailing the sample to a laboratory (which can take a few days), and waiting for the results of extraction, amplification, sequencing, and analysis (which can take about 42 days)—thus, this traditional analysis can take about 53-55 days in total. In contrast, using an aspect of the present teachings involving image analysis of a biological sample such as a stool sample, a user may capture a photo of stool at their convenience using a smartphone or the like and upload the photo (or otherwise transmit a digital photo file) for analysis, where the computer-implemented analysis is performed and data is ready for the user within seconds—the entire process can take less than 1 minute, e.g., 30 seconds or less, 15 seconds or less, or even 5 seconds or less. In an embodiment, the user may repeat the technique outlined above at a later time to attempt to optimize a preexisting health plan and/or preexisting personalized dietary supplement and/or measure/quantify health outcomes as a function of the new health plan. Furthermore, the present teachings may be used as a viable alternate means of delivering a personalized health insight based on an analysis of specimens to which there is no corresponding laboratory analysis—e.g., mucus.

Figure 7:
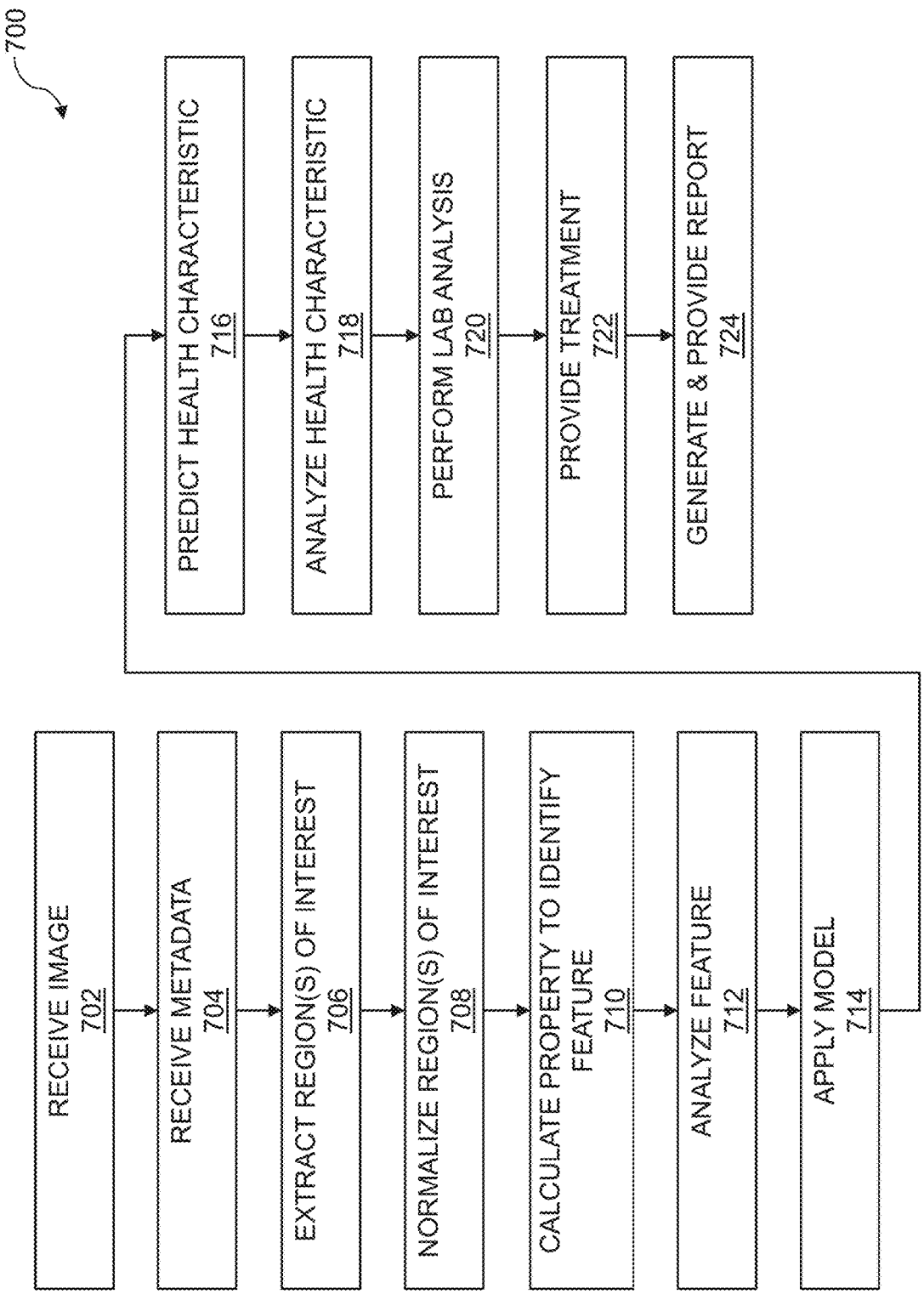
FIG. 7 is a flow chart of a method of analyzing an image to provide a health assessment of an animal, in accordance with a representative embodiment.

FIG. 7 is a flow chart of a method of analyzing an image to provide a health assessment of an animal, in accordance with a representative embodiment. The method 700 may be performed using any of the systems and techniques described herein, alone or in combination, e.g., the system 100 of FIG. 1. By way of example, the method 700 may include analyzing an image of a stool sample containing mucus to provide a health assessment of the animal that excreted the stool sample with mucus. However, and similar to other aspects of the present disclosure, it will be further understood that while the method 700 may emphasize the use of an image of a stool sample for analysis, the method 700 may be employed using an image of another form of a biological sample, such as any as described herein. Regardless, in general, the method 700 may include the submission of a photo of a biological sample (e.g., a digital file containing the photo), the processing and analyzing of that photo, and providing useful feedback related to health in view of that analysis.

As shown in step 702, the method 700 may include receiving an image, where the image includes a biological sample of an animal. For example, the image may include a digital photograph of a stool sample that was excreted by the animal, where the stool sample contains mucus or the like. In this manner, in a preferred embodiment, the image includes a photo from a smartphone or other web-enabled device (e.g., a digital photograph) that is transmitted to a platform for analysis (e.g., transmitted over a data network to a remote computing resource for processing and analysis). However, other forms of receiving an image are also or instead possible. For example, the image may be stored in a database, where receiving the image may include retrieving the image from the database, whether local or remote to a computing resource that performs processing of the image.

It will be understood that, in addition to or instead of receiving an image, the method 700 (or an aspect of the present teachings more generally) may include receiving one or more of a video, a plurality of images, a three-dimensional scan, and the like. For example, in this context, a video can simply be thought of as a collection of still images, where one or more of these images may be analyzed as described herein. This can yield more input data for an aspect of the present teachings, and thus more-refined results/recommendations. For example, a video or the like can provide more angles, views, colors, features, and the like of a biological sample for image-based analysis. Thus, as described herein, an image being analyzed will be understood as potentially including one or more of a video, a three-dimensional image, and the like, or a portion thereof—e.g., a still image or other portion of a video, scan, or the like.

As shown in step 704, the method 700 may include receiving metadata, e.g., metadata associated with the image, a user, the animal, or otherwise. In some implementations, the image itself includes metadata—e.g., a file containing the image, a file name, a file directory and/or directory structure, and the like. For example, in this manner, the metadata may include one or more of a time, a date, a geographic location or other geolocation information, other metadata commonly associated with a digital photograph or computer file generally, and the like. The metadata may also or instead include other information such as a questionnaire response related to one or more aspects of the animal—e.g., a health, a behavior, a current diet, a supplement, a medication, ethnographic information, a breed, a weight, a size, other physiological information, and the like. The metadata may also or instead include laboratory data or the like. For example, the metadata may include bloodwork analysis, DNA gene sequencing on the animal, results of a microbiome analysis for the animal's stool, results of a metabolome analysis for the animal's stool, and the like. The metadata may also or instead include historical data—e.g., data from previous analyses of a biological sample of the animal or analyses related to another animal. This historical data may include raw data and/or derived data.

The metadata may also or instead include information that can be used to test and/or reinforce some of the model analysis techniques of the method 700. For example, the metadata may include a ground truth attribute such as a weight of the biological sample and/or a clinical diagnosis such as irritable bowel syndrome when the biological sample is (or contains) a mucus sample. Such a ground truth attribute may also or instead include manually segmented images in the semantic segmentation algorithm.

As shown in step 706, the method 700 may include identifying and extracting one or more regions of interest within the image for further analysis. These regions of interest may include at least a first region of interest having only the biological sample therein. For example, in an aspect where the biological sample contains mucus, one or more of the regions of interest may include at least a first region of interest having only the mucus therein. When this is the case—i.e., when only the biological sample is present within the region of interest and the region of interest can be identified and extracted for processing—normalization of the region of interest may be unnecessary. However, an aspect of the method 700 may include normalization as explained in more detail below with reference to step 708.

As described herein, in certain aspects, the image includes a background distinct from the biological sample, and thus one or more regions of interest may include a second region of interest having at least a portion of the background therein. In this manner, extracting one or more regions of interest may include identifying the biological sample and the background within at least a portion of the image. In some instances, the background in this context includes a portion of the biological sample—e.g., where the biological sample is stool that contains mucus, and where mucus is being analyzed in the first region of interest, the second region of interest may include background that includes stool. The method 700 may further include creating the first region of interest based on an identification of only the biological sample, and creating the second region of interest based on an identification of both a portion of the biological sample and a portion of the background. Also, or instead, the method 700 may include classifying the first region of interest and the second region of interest for separate analysis thereof. For example, the second region of interest may be stool from the same bowel movement that produced the mucus excrement that is being analyzed in the first region of interest, e.g., where there is an advantage to an analysis of each of the first region of interest and the second region of interest.

In certain aspects, the images that are received or otherwise retrieved for systems and techniques of the present teachings can be highly variable. For example, lighting and background conditions can vary significantly from image to image. For example, lighting and background conditions can vary significantly from image to image. By way of example, simple image analysis (e.g., Otsu's threshold and segmentation) may not work well due to the presence of highly variable backgrounds, which is why a U-Net network may be preferred—i.e., a version of a semantic segmentation network that is often used in biomedical imaging applications. Convolutional neural networks may require certain pre-processing as a way to standardize the images and/or regions thereof for analysis. Thus, in an aspect, images may be resized and/or normalized for consistency in inputs where a U-Net network is used. Also or instead, a model used herein for such segmentation may be improved with data augmentation, k-folding, more data, other semantic segmentation networks and training patterns, manually segmented images, combinations thereof, and the like.

Extracting a region of interest may thus include segmentation. For example, extracting one or more regions of interest may include a segmentation of the image performed at least in part by a model—e.g., a segmentation model or a portion of a model configured to perform more comprehensive analysis. One or more of these models may include a deep learning model. In this manner, in an aspect, extracting one or more regions of interest may include an automatic segmentation of the image, where such an automatic segmentation includes utilizing one or more semantic segmentation models using deep learning. For example, a semantic segmentation model used herein may include a U-Net network. Also or instead, a semantic segmentation model used herein may be used with at least one of data augmentation, k-folding, and an additional input of data. Ground truth data may be used as an input in a semantic segmentation model to train and validate the model. Thus, semantic segmentation network models can be trained internally (e.g., U-Net) and/or adapted from public models using transfer learning to perform image segmentation. And ground truth data (e.g., with all classes labeled) can be provided as inputs to help train/validate the model for optimal accuracy.

Extracting a region of interest may also or instead include a manual segmentation of the image. In this manner, in an aspect, extracting one or more regions of interest includes a combination of a manual segmentation of the image and an automatic segmentation of the image. For example, images may be manually segmented when the dataset is relatively small. Manual segmentation may help improve a signal to noise ratio (SNR) of features extracted, since regions of interest should theoretically be well-defined. Regardless, in an aspect, automatic ROI segmentation is performed using semantic segmentation models using deep learning, which can provide high-quality, autonomous region-of-interest segmentation.

The output from the extraction of one or more regions of interest may include regions of interest that are classified as one of biological sample only, background only, or a combination of biological sample and background.

As shown in step 708, the method 700 may include normalizing one or more regions of interest of the image. Images may be normalized to control for different image acquisition settings (e.g., focal lengths, magnification, and the like). Also or instead, color and length features of the biological sample may be extracted and/or normalized, e.g., using markings on a known background as correction factors to apply to certain regions of interest. For example, the image may include a background that is distinct from the biological sample, where normalization is performed to analyze only the biological sample in a useful manner. Thus, one or more of the regions of interest may include a second region of interest having at least a portion of the background therein. By way of example, in an aspect where the biological sample includes a mucus sample, the background can include one or more of a surface (e.g., a man-made surface such as concrete, or a natural surface such as grass) and/or the background can include a bag, container, or the like that holds or otherwise contains the mucus sample. As explained above, the background can also or instead contain relevant image substrates, including stool by way of example. Additionally or alternatively, and as explained in more detail below, the background may include predetermined markings or features that can aid in one or more of normalization, extracting and identifying a region of interest, extracting and identifying features of a biological sample, and so on. In some aspects, the background can include several types of backgrounds, e.g., a combination of one or more of a surface specifically tailored for image analysis, grass, dirt, debris, concrete and/or pavement, and the like.

In this manner, the method 700 may include normalizing one or more of a first region of interest including only the biological sample and a second region of interest including some background, thereby creating a normalized image for further standardized analysis. It will be understood that the second region of interest can purposefully include some background to account for image variability and/or because it may include additional metadata that may be combined to create a more holistic health determination and thereby a more precise health recommendation. For example, where mucus content is being analyzed on a stool sample, an analysis of the stool itself (separate from the mucus analysis) can provide value for a health recommendation, particularly when combined with the mucus analysis. Identifying one or more features of the biological sample as explained herein may thus occur by analyzing this normalized image.

In an aspect, normalizing one or more regions of interest includes extracting normalization factors, such as a color attribute and a dimensional attribute (e.g., a length) of the biological sample from the second region of interest that includes at least a portion of the biological sample and at least a portion of a background. As mentioned above, the background may be strategically designed to assist in the normalization process, or otherwise for analysis of the biological sample—e.g., in an aspect, the background includes a resting surface having predetermined markings thereon. For example, the background may include a sheet (e.g., a plastic sheet, which can be in the form of a bag for collecting and/or disposing of stool) or another surface with markings that can be used for normalization. Thus, a marking on the background in the second region of interest may be used for extracting one or more of the color attribute and the dimensional attribute. The marking may include symbols, designs, or text having known attributes. In this manner, the marking may have one or more of a known size and a known shape (e.g., rectangles, triangles, circles, lines, waves, or the like, having known dimensions). The marking may also or instead include one or more alphanumeric characters—e.g., letters and/or numbers. By way of example, if the markings on a background within an image include characters with known sizes, an aspect ratio of the characters may be used to calculate dimensions of contents within the image. Use of the aspect ratio may be applied from an image analysis perspective, e.g., where the method 700 may include identifying how many pixels correspond to a set distance so that techniques can convert from raw calculations in pixels to a more useful form. The marking may also or instead include one or more colors, e.g., a plurality of colors. In this manner, the colors of the markings can provide a baseline reference for determining colors within the biological sample, which can assist in accounting for image acquisition differences (e.g., one or more of lighting, focus, magnification, and the like).

Normalizing one or more regions of interest may further include calculating a correction factor for a color and an aspect ratio using the extracted color attribute and the extracted dimensional attribute, and applying the correction factor to the first region of interest. Normalizing one or more regions of interest may also or instead include a resizing of a region of interest.

Normalizing one or more regions of interest may account for one or more image acquisition settings used in capturing the image, e.g., settings of a camera application on a user's smartphone or the like. Such an image acquisition setting may include one or more of a focal length, a color setting, a lighting setting, a magnification, and the like.

As shown in step 710, the method 700 may include calculating one or more attributes, including but not limited to a geometric attribute, an opacity attribute, a texture attribute, and/or a color attribute in the first region of interest to identify one or more features of the biological sample. For example, in an aspect, the method 700 may include calculating each of a geometric attribute, a texture attribute, and a color attribute in the first region of interest to identify one or more features of the biological sample.

The features that are identified in this step 710 may include at least one of a color, a texture, a number of binaries, an area (e.g., the number of pixels that the sample occupies), a perimeter (e.g., the perimeter of the sample that approximates the contour as a line through the centers of border pixels using an 8-connectivity, a 4-connectivity, and the like), a circularity (e.g., a measure of how similar the shape of the sample is to a circle), a volume, a mass, an eccentricity (e.g., a measure of an aspect ratio computed to be the eccentricity of the ellipse that has the same second moments as the sample region), a major axis (e.g., the length of the major axis of the ellipse that has the same normalized second central moments as the sample), a minor axis (e.g., the length of the minor axis of the ellipse that has the same normalized second central moments as the sample), a minor-major-axis ratio (e.g., a measure of the aspect ratio of these axes, meaning the ratio of the minor to major axes of the ellipse that has the same second moments as the sample region), a viscosity, a consistency, a moisture content, a solidity (e.g., a measure of the convexity computed as the ratio of the number of pixels in the sample to that of its convex hull), an extent (e.g., a ratio of an area of the sample to its axis-aligned bounding box), an equivalent diameter (e.g., the diameter of a circle with the same area as the sample), a specularity, a coherence, a reflectance, a diffusivity, a presence of substance that is distinct from the biological sample (e.g., a non-stool substance when the biological sample is a stool sample, such as a foreign object or biological matter like mucus), and the like. It will be understood that the features that are identified in this step 710 may include derived features. By way of example, viscosity may be modeled and then derived prior to feature engineering.

For example, mass may be identified in step 710. In an aspect, the mass is calculated from a geometry and a texture attribute of the biological sample. Also or instead, the mass may be calculated from at least one of a color and a derived color vector of the stool sample. In an aspect, a mass model may be implemented in the method 700, where such a model uses features including but not limited to color and geometry attribute vectors (x) and ground truth weights from metadata as labels (y). In an aspect, the same test train split procedure may be used to train the model on about 80% of the data and to evaluate the model's performance with the remaining about 20%. With the training data, supervised machine learning regression algorithms (e.g., support vector machines, k-nearest neighbors, random forest regressor, and the like) may be used to predict the continuous output (which can be chosen to get a weight output instead of categorical Bristol stool score labels or the like). These models may then be optimized using hyperparameter search routines such as one or more of 'gridsearch,' 'randomsearch,' and the like.

By way of further example, and as mentioned above, where the biological sample is a mucus sample, one or more features of the mucus sample may include the presence of the non-mucus substance in the form of stool. In this manner, the non-mucus substance may also or instead include a foreign object—e.g., one or more of a parasite, a pathogen, an inanimate object such as a toy, and the like. Moreover, the converse may also or instead be true—where the biological sample is a stool sample, one or more features of the stool sample may include the presence of the non-stool substance in the form of mucus.

As discussed above, the method 700 may include calculating a color attribute in a region of interest (e.g., the first region of interest) to identify one or more features of the biological sample. By way of example, in an aspect, an output of the method 700 may include a health characteristic in the form of a classification on the Bristol stool scale, where this classification is based at least in part on the color attribute. The color attribute may also or instead be used at least in part for determining an attribute related to consistency, which may be particularly applicable in the context of a stool sample.

The color attribute may be derived from or otherwise utilize one or more of a red-green-blue color model, a red-green-blue-alpha color model, a hue-saturation-value color model, and/or a CIELAB color model. Also or instead, the color attribute may be calculated using a multidimensional color plane. Such a calculated-multidimensional color plane may be provided using an algorithm such as a k-means algorithm. By way of example, the color attribute may be calculated using a dimensionality reduction approach (e.g., k-means clustering) to cluster regions of similar colors. For example, segmenting ten color planes within a stool ROI may allow techniques to look at color homogeneity within a sample (e.g., color plane 1 may have 30% abundance and be the dominant color cluster). These homogeneity values can be further used as features for training several machine-learning models.

As discussed above, the method 700 may include calculating a geometric attribute in a region of interest (e.g., the first region of interest) to identify one or more features of the biological sample. In an aspect, calculating the geometric attribute includes converting the first region of interest to grayscale, converting the first region of interest to binary, and applying one or more morphological operations to the first region of interest.

As discussed above, the method 700 may include calculating a texture attribute in a region of interest (e.g., the first region of interest) to identify one or more features of the biological sample. In certain implementations, calculating the texture attribute includes use of a gray level co-occurrence matrix (GLCM), where GLCM is a statistical measure that measures spatial relationships between patterns of contiguous pixels. Use of the GLCM may include plotting a plurality of points for identifying a cluster thereof. Thus, it will be understood that one or more features of the biological sample that are identified through calculation of a property from the image may not be human visual, and the texture attribute is one example where GLCM is used to extract this attribute. By way of further example, texture can also or instead be calculated using a Gabor filter bank, which includes permutations of different magnitude, orientation, and frequencies of Gabor wavelets. Each Gabor wavelet may be convolved over an image and may create a filtered image, with high signal captured from texture or oriented pixels in phase with the Gabor filter. And these filtered images can be used for the classification of texture. The following is a publicly available script that shows how this sequence can be adapted and executed in the context of the present teachings—https://scikit-image.org/docs/stable/auto_examples/features_detection/plot_gabor.html—and one skilled in the art would understand how to implement such a technique given the present disclosure.

Thus, many feature sets can be calculated from the images, where four example feature sets include color, opacity, texture, and region properties, which can be calculated at respective points in an analysis pipeline. These feature sets can be used for training a machine learning model. An example analysis pipeline to identify these features may include converting an image to grayscale, and calculating texture properties therefrom. That grayscale image may then be converted to binary, and have its signal cleaned with morphological operations (e.g., erosions/dilations) for calculating region properties. The image may have global color vectors calculated to get the color attribute and related features. In this manner, output of this step 710 may include one or more of a color, an opacity, a texture, a number of binaries, an area, a circularity, an eccentricity, a major and minor axis, a perimeter, and the like.

As shown in step 712, the method 700 may include analyzing one or more features of the biological sample—e.g., the features identified from calculating one or more of the geometric attribute, the opacity attribute, the surface area coverage attribute, the texture attribute, and the color attribute. For example, this step 712 may include analyzing a feature of the biological sample in view of a reference database to determine a health characteristic of the animal or a treatment for the animal. The reference database may be a historical database that includes data from analyses of other biological samples—e.g., biological samples from the same animal or biological samples from different animals.

It will be understood that steps 710 and 712 described above may be omitted when employing deep learning generally (e.g., using a CNN) rather than classical machine learning. To this end, when using a CNN or the like, one or more of the regions of interest that is identified, extracted, and/or normalized in the method 700 may simply be inputted into the model when using deep learning. Thus, in certain implementations, the method 700 may move directly from step 708 to step 714.

As shown in step 714, the method 700 may include applying a model to one or more features of the biological sample. In general, the model may be part of a recommendation engine configured to provide one or more recommendations for a treatment in view of a health characteristic determined or identified in the analysis of the image of the biological sample. That is, the model may be configured to (e.g., programmed to) predict a health characteristic of the animal from which the biological sample originated (e.g., where the biological sample is mucus, the model may predict a health characteristic of the animal from which the mucus originated). It will be understood that, in the context of the present teachings, the "model" may include output by one or more algorithms that can be comprised of model data and a prediction algorithm. Thus, the algorithm may be thought of as the programming, and the models may be thought of as representing the program. In this manner, the models discussed herein in the context of the present teachings may represent what was learned by one or more machine-learning algorithms. The model may thus represent output that is saved after running a machine-learning algorithm on training data and can represent the rules, numbers, and any other algorithm-specific data structures required to make predictions. Thus, the model may include both data and a procedure (as set forth by one or more algorithms) for using the data to make a prediction. Therefore, in the context of the present teachings, a model may learn patterns in the input data (e.g., a color, geometry, opacity, texture, surface area, presence or absence of a substance such as mucus, and the like) and the model may abstract these patterns into relationships (e.g., mathematical functions), such that, when new data is entered, the "model" uses these functions it has learned with the training data to create a prediction (e.g., a health characteristic prediction for formulating a treatment plan).

The model may include a machine-learning model. In general, the machine-learning model may be the output of one or more machine learning algorithms running on input data—e.g., input data in the form of an identified feature of the biological sample from the processing of the image of the sample as described herein. The machine-learning model may utilize an algorithm configured to perform pattern recognition, such as described above.

The model may include a probabilistic model, e.g., a stochastic model or the like. Probabilistic models may yield a stochastic chance for an instance to occur. By way of example, this can include the temporal tracking of health data (similar to a time series analysis) where models (e.g., recurrent neural network such as long short-term memory (LSTM)) are used to forecast future chances of a health outcome.

The model may apply one or more of a weight and a score to a feature of the biological sample for predicting the health characteristic. The weight and/or the score may be customized for the animal that is associated with the biological sample. It will be understood that these weights and/or scores may be tailored for use by a specific model, and/or they can be tailored for use by more than one model (e.g., where models are interconnected).

It will thus be understood that one or more of the models used herein may be interconnected within another one or more models. For example, several machine-learning models can contribute towards a health prediction (e.g., a mucus model including opacity, thickness, surface area, and so on). In an aspect, the aforementioned weights can provide for an expected average of each individual model's predictions. Thus, the weights described herein may include one or more of individual model weights (e.g., a color model may be a linear regression—y=mx+b—where the weights are 'm' and 'b' values) and weights of an expected average as just described (e.g., health index=a*consistency prediction+b*color prediction). Stated otherwise, a model used in the present teachings may be made up of several models (e.g., a comprehensive model may include one or more of a color model, a consistency model, and so on), where model weights may assist in computing an expected average, whereas the model weights in an individual model (e.g., the color model) may be used for training/executing that particular model.

Therefore, it will also be understood that one or more models may be input to another one or more models. For example, an opacity model and a surface area model (which can be included as part of a mucus model) may each make a prediction for a mucus health score in an aspect. In this example, the expected average of these two values may be used to create the health index score. And this predicted mucus health score value may then be provided as an input to a health model to predict animal health.

In this manner, the present teachings may include a system of models, which refers to a combination and/or a collection of individual models, e.g., to make a determination on a derived metric, such as "overall health score" and the like. Thus, it will be understood that the models may include individual models and/or ensemble models, e.g., where, in ensemble models, the strengths of each model are considered to provide a final derived outcome. That is, it will be understood that a system of models can be generated using individual models as components (e.g., inputs to the system of models). For example, an individual support vector machine model for geometric attributes and a separate individual linear regression model for color attributes can be defined, where each model can be trained to predict a health outcome, such as mucus health score. A system of these two models can be defined such that both individual models contribute together to predict a health outcome, such as mucus health score. Moreover, an additional system of models can be created when the output of one individual model (e.g., mucus health score prediction of a geometric model or other model) is used as a feature for a separate model (e.g., a microbiome prediction model).

An aspect of the present teachings may also or instead include training one or more models, e.g., for use in step 714 of the method 700. In certain aspects, training the model includes using one or more features of the biological sample that were identified in the image analysis. A few examples of training the model in the context of the biological sample including mucus are included below, but it will be understood that other techniques may also or instead be used to train the model(s) herein.

Training the model may begin with data wrangling to prepare for actual training. For example, in the context of the biological sample including mucus, various mucus health features may be retrieved or otherwise gathered. This may include extracting data from a source, including a spreadsheet, a relational and/or non-relational database (stored locally or remotely, e.g., on the cloud), and the like. This may include loading the data into software, and transforming data as needed (e.g., scaling data to unit mean and variance, and the like). Data can continue to be cleaned prior to analysis (e.g., via one or more of string formatting, removing null values, converting object types, and the like). This may further include formatting feature matrix X and label vector Y, where feature matrix X can have any number of features, including region properties, color, and so on, and where feature vector y contains a true class label (e.g., mucus presence or absence).

Preparation of data for training may also include semantic segmentation. As such, ground truth labels may first be created, where these can be created manually. Next, images and corresponding ground truth labels may be stored in a data source (e.g., local or remote, e.g., on a cloud-based storage system). Images may be extracted from a source (e.g., local or cloud-based storage), resized to standard sizes, and augmented. Such augmentation may include one or more of cropping, flipping vertically/horizontally, shearing, rotating, and the like. This can be done to increase the dataset size to both raw and ground truth images. It will be understood that the preparation of data for training could be automated with software.

Continuing with this training example, the modeling will now be discussed. Training the model may include training to identify health features and the like based on identifying and analyzing mucus and the like. To this end, the train test may be split to train the model—e.g., use a portion of data (~70-80%) to train the model; reserve some data (~20-30%) to test the data after training; and for validating (~10%) the model during training. The model may be created, e.g., loaded from a package or a custom defined architecture. The model may then be trained using training data. For this, one can optionally feed in validation data to validate during training. Model accuracy may be evaluated with testing data to compare predictions to ground truth data. Model hyper-parameters can be optimized using routines like cross-validation, grid search, and so on, to propose the best parameters leading to highest accuracy, lowest bias, and/or lowest variance. The model can be saved to be called at runtime, where the model may have an application programming interface (API) to be called programmatically at runtime.

Training the model may also or instead include sematic segmentation training, which may follow a similar procedure as that described above. Thus, one may define a custom convolutional neural network (CNN) architecture or instantiate CNN architecture (e.g., U-Net). The data set may be split to train the model—e.g., use a portion of data (~70-80%) to train the model; reserve some data (~20-30%) to test the data after training; and for validating (~10%) the model during training. The model may then be trained using training data. For this, one can optionally feed in validation data to validate during training—e.g., evaluate model accuracy with testing data comparing predictions to ground truth (e.g., DICE coefficients). Model hyperparameters can be optimized using routines like cross-validation, grid search, and so on, to propose the best parameters leading to highest accuracy, lowest bias, and/or lowest variance. The model can be saved to be called at runtime, where the model may have an API to be called programmatically at runtime.

Training the model may also or instead include training a model to identify a feature in mucus. To this end, pre-trained, open source, model weights (e.g., VGG-16) may be loaded, which may have been previously trained on several million images. The weights may then be adapted for the context of the present teachings.

Image class metadata may be passed in, which can be organized by folder name, and/or passed as a dictionary/list object with corresponding class names per image. The train test may be split to train the model—e.g., use a portion of data (~70-80%) to train the model; reserve some data (~20-30%) to test the data after training; and for validating (~10%) the model during training. The model may then be trained using training data. For this, one can optionally feed in validation data to validate during training—e.g., evaluate model accuracy with testing data comparing predictions to ground truth (e.g., DICE coefficients, labels passed in folder structure metadata, and the like). Model hyperparameters can be optimized using routines like cross-validation, grid search, and so on, to propose the best parameters leading to highest accuracy, lowest bias, and/or lowest variance. The model can be saved to be called at runtime, where the model may have an API to be called programmatically at runtime.

As mentioned above, other training techniques are also or instead possible for training one or more of the models described herein. It will also be understood that, where a model is described as performing an action or function, this may include a single model or a combination of a plurality of models.

An output of the model may yield a usable input for predicting a health characteristic as described herein. For example, output of the model may include a mucus grade corresponding to an amount of mucus present in a region of interest. Such a grade may identify the amount of mucus as one of absent, low, or high—although other scales could certainly be used as will be understood. Output of the model may also or instead include one or more labels corresponding to characteristic of a region of interest or a substance contained therein, e.g., mucus or the like. In this manner, output of the model may include one or more labels corresponding to an opacity of mucus present, a thickness of mucus present, a surface area occupied by mucus, a color of mucus present, an estimate of microbial content of mucus present, an estimate of a level of cortisol in the host animal, an estimate of a level of bacteria, detection of blood, detection of a pathogen, combinations of any of the foregoing, and the like.

As shown in step 716, the method 700 may include, based at least in part on the output of the model, predicting a health characteristic of an animal from which the biological sample originated. The health characteristic as described herein may be any attribute useful for sustaining or improving the health and well-being of the animal, and/or any characteristic that could identify a potential health issue. For example, as discussed herein, in an aspect where the biological sample is a mucus sample, the health characteristic may include a classification on a mucus health scale, prediction of cortisol levels in the host animal, prediction of bacteria levels, detection of blood and/or pathogens, and the like.

As shown in step 718, the method 700 may include analyzing one or more health characteristics predicted by the model, i.e., a health characteristic of the animal associated with the biological sample. For example, this step 718 may include analyzing a health characteristic in view of a reference database to determine a treatment for the animal associated with the biological sample. The reference database may be a historical database that includes data from analyses of other biological samples—e.g., biological samples from the same animal or biological samples from different animals.

As shown in step 720, the method 700 may include performing a laboratory analysis or another analysis of the biological sample separate from the image analysis described above. This analysis may be used as a factor in predicting the health characteristic of the animal. Also, or instead, this analysis may be used to test the image analysis techniques described above, and/or for providing ground truth data. By way of example, when the biological sample includes a mucus sample, this step 720 may include performing microbiome DNA gene sequencing on the mucus sample (e.g., of either the host organism and/or the gastrointestinal microflora (aka microbiome)). To this end, the method 700 may further include applying results from the microbiome DNA gene sequencing as a factor in predicting the health characteristic of the animal. Also, or instead, when the biological sample includes a mucus sample, this step 720 may include performing metabolomics sequencing on the mucus sample. To this end, the method 700 may further include applying results from the metabolomics sequencing as a factor in predicting the health characteristic of the animal.

Step 720 may also or instead include performing further analysis such as one or more of mass spectroscopy, conductance, and rheology, e.g., when the biological sample includes a mucus sample. Again, results of this further analysis may be used as a factor in predicting the health characteristic of the animal and/or for training a model.

As shown in step 722, the method 700 may include providing a treatment for the animal, e.g., in view of the health attribute that was at least in part predicted by the applied model. The treatment may include one or more of a food, a liquid, a supplement, a behavior recommendation (e.g., sleep, exercise, enrichment, and the like), and/or a medicine. For example, the treatment may include a personalized dietary supplement for the animal. Such a personalized dietary supplement may include a predetermined amount of one or more of a probiotic, a prebiotic, a digestive enzyme, an anti-inflammatory, a natural extract, a vitamin, a mineral, an amino acid, a short-chain fatty acid, an oil, a formulating agent, and the like.

Thus, an embodiment executing the method 700, or any of the methods disclosed herein, may be used to obtain a personalized dietary supplement for the animal. A personalized dietary supplement may include, but is not limited to, personalized ingredient levels of beneficial ingredients, which can be combined with formulating agents where applicable. In this manner, a personalized supplement system may be provided by the present teachings. Such a personalized supplement system may include a durable container structurally configured for storing the personalized dietary supplement, where the container may be generally sized and shaped for easy refills. Refill cups may also be provided, where these may be recyclable and structurally configured for easy use and fill. A supplement spoon or the like may be used, where such a spoon may be custom-designed to contain a dose that is personalized for an animal's specifications. This system can ensure compliance of dosing a personalized dietary supplement. Also or instead, the personalized supplement system may include a subscription service or the like, where supplements are mailed or otherwise delivered to an end-user on a predetermined basis and/or in predetermined doses. For example, a packet or other container may be used to store a pre-dosed amount of a personalized supplement to be added to the animal's food or water, where one or more of these packets are supplied to an end user on a predetermined basis.

The treatment may also or instead include a customized health plan for the animal. The customized health plan may include one or more of a behavioral change, a dietary change, and the like. The customized health plan may also or instead include a recommendation regarding one or more of diet, sleep, exercise, an activity, enrichment, a lifestyle change, and the like.

As shown in step 724, the method 700 may include generating and providing a report for the animal, e.g., where the report includes information regarding the health characteristic predicted by the model.

The method 700 described above may be performed using one or more computing devices. To that end, the present teachings may include a computer program product for analyzing a biological sample image to provide a health assessment of an animal, the computer program product comprising computer executable code embodied in a non-transitory computer readable medium that, when executing on one or more computing devices, performs the steps of: receiving an image, the image including a biological sample containing mucus; identifying and extracting one or more regions of interest within the image for further analysis; applying a model to one or more of the regions of interest to identify one or more conditions of mucus therein, the model trained using a plurality of images having varying conditions of mucus, where output of the model includes at least a grade corresponding to an amount of mucus present in the one or more regions of interest; based at least in part on the output of the model, predicting a health characteristic of an animal from which the biological sample originated; and presenting the health characteristic to a user associated with the animal.

Figure 8:
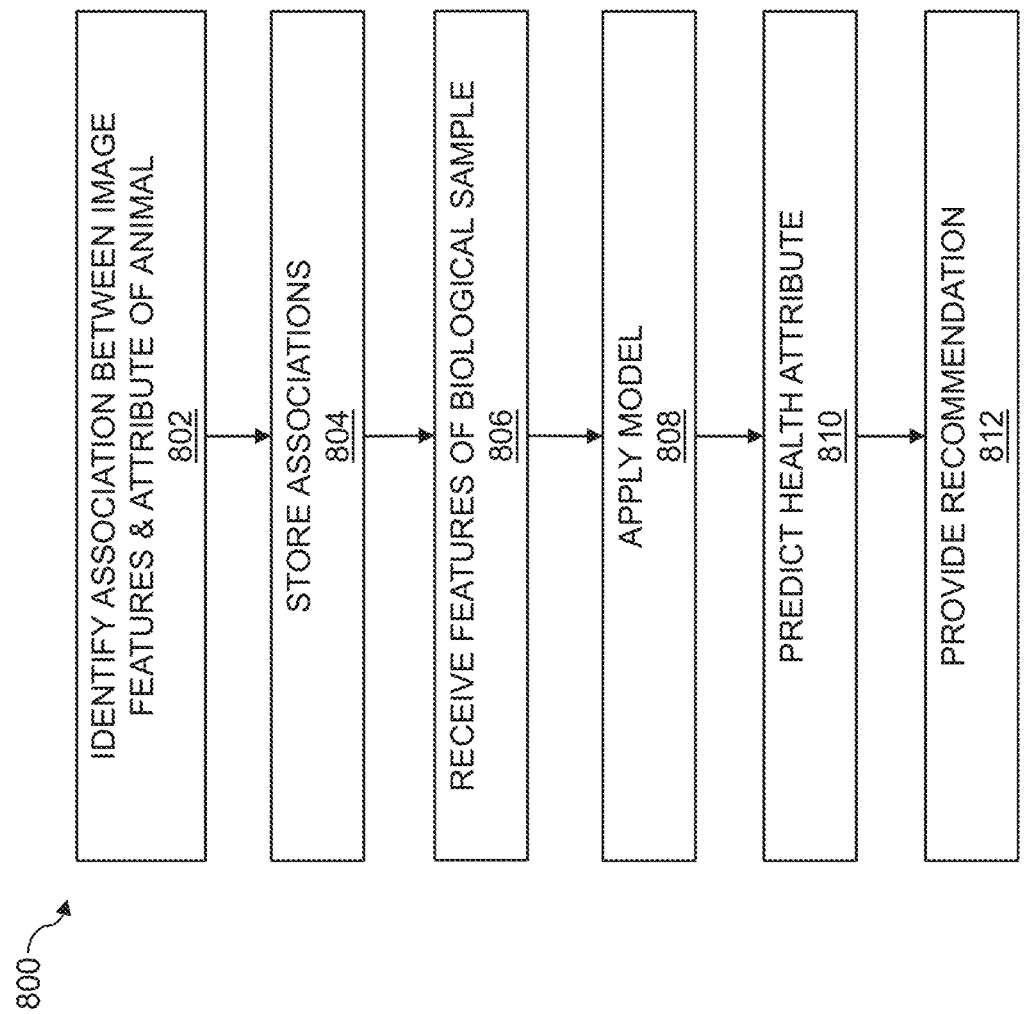
FIG. 8 is a flow chart of a method of analyzing an image to provide a health assessment of an animal, in accordance with a representative embodiment.

FIG. 8 is a flow chart of a method of analyzing an image of a biological sample to provide a health assessment of an animal, in accordance with a representative embodiment. In general, the method 800 may utilize a model (e.g., a correlation model), which may be the same or similar model trained as per the description of FIG. 5. As such, the method 800 of FIG. 8 may be similar to the technique described with reference to FIG. 6, where it will be understood that steps of these techniques may be substituted and/or supplemented for one another.

As shown in step 802, the method 800 may include identifying one or more associations between (i) one or more features and/or other data ascertained from an analysis of an image of a biological sample and (ii) one or more attributes and/or characteristics of an animal that is associated with the biological sample.

Thus, this step 802 may also or instead include identifying one or more features of a biological sample contained in an image. Thus, the features or other data ascertained from an image of a biological sample may be discovered, uncovered, calculated, and/or identified from one or more of the various image analysis techniques described herein—e.g., performed on a digital photograph of the biological sample. By way of example, such features may include those which are identified and trained by a convolutional neural network, such as RESNET-18.

The attributes and/or characteristics of an animal that are associated with the biological sample may include the presence or absence of a substance (e.g., one or more of a microbiome characteristic and a metabolome characteristic), a health characteristic, a score (e.g., a mucus health score), and the like, including combinations thereof. By way of example, such attributes and/or characteristics may include, or otherwise assist in the identification of, one or more of an indication of diet (e.g., carbohydrate intake, fresh food intake, protein intake, fat intake, metabolism thereof, and so on), an indication of metabolism, an indication of weight of the animal, an indication of a health condition or sickness (e.g., cancer, irritable bowel syndrome (IBS), obesity, and so on), pathogen presence or absence, parasite presence or absence, cortisol levels in the host animal, and the like. It will be understood that the presence of one substance may indicate the presence or absence of another substance, and vice-versa—where such inferences can be readily included in the present teachings.

By way of example, some possible associations will now be described in the context of a mucus sample—i.e., correlations from image features and health-related attributes and/or characteristics such as the presence or absence of a gastrointestinal microbiome characteristic. The opacity of a mucus sample can have a correlation to the mean concentration of bacteria within the mucus, which can lead to a further indication of dysbiosis, which can be helpful for dietary recommendations. In this manner, if the opacity is relatively high, this can indicate a presence of an imbalance of the microbiome, which can infer a relatively high level of digestive distress and lead to a recommendation of probiotics, antibiotics, mucosal agents, demulcents, and the like. The surface area or percentage coating of mucus on a stool substrate or the like can have an association with the host organism's immune response to protect from uptake, which can lead to a recommendation for detoxification and/or additional pathogen testing, among others. The color of mucus can have an association with the integrity of the intestinal lining—for example, a red color can indicate the presence of blood, which then can indicate a compromised intestinal lining, which can lead to a recommendation for immediate medical attention.

By way of example, further possible correlations will now be described in the context of a stool sample—i.e., correlations from image features and health-related attributes and/or characteristics such as the presence or absence of metabolome subsystems. The eccentricity can have a correlation to the presence or absence of one or more metabolites indicating carbohydrate intake, virulence, disease, and defense. The equivalent diameter can have a correlation to the presence or absence of one or more metabolome sub-systems indicating carbohydrate intake, amino acids and derivatives, protein metabolism, cofactors, vitamins, prosthetic groups, pigments, virulence, disease, and defense. Other correlations are also or instead possible.

As shown in step 804, the method 800 may include storing the associations (e.g., the correlations described above) or otherwise making them available to a model (e.g., a correlation model). For example, associations may be stored in a reference database accessible to the model.

As shown in step 806, the method 800 may include receiving one or more features of a biological sample (e.g., a stool sample containing mucus) calculated from one or more regions of interest within an image including the biological sample. The features may relate to at least one of a geometric attribute, an opacity attribute, a color attribute, a texture attribute, and the like, of the biological sample. It will be understood that one or more of these attributes may be derived attributes. For example, where the features relate to a color attribute, such a color attribute may include one or more of a color and a derived attribute related to the color (e.g., using k-means color segmentation for calculating color homogeneity, where derived features are created). In a more simplistic example, certain colors can derive a dietary attribute, such as an intake of a particular food or substance.

It will also be understood that these features may be comprised of thousands of attributes as defined by a deep learning algorithm, which cannot be constructed or defined by human constructs. Stated otherwise, when using classical machine learning, the model may need a starting place of what to look for within input images, and thus the method 800 may include a step 806 of receiving the features as described above. However, when using deep learning with a CNN or the like, the model itself may be able to find features of interest entirely based on its training, e.g., using millions of images.

As shown in step 808, the method 800 may include applying a model to a feature of the biological sample and the number of associations to determine useful insight regarding the animal.

The method 800 may also or instead include training the model, e.g., using hundreds of datapoints. After a model 800 has been trained, it may be loaded to receive inputs such as the image features described herein.

As shown in step 810, the method 800 may include predicting a health characteristic of an animal associated with the biological sample.

As shown in step 812, the method 800 may include providing a treatment (which may include a recommendation) in view of the health characteristic.

Figure 9:
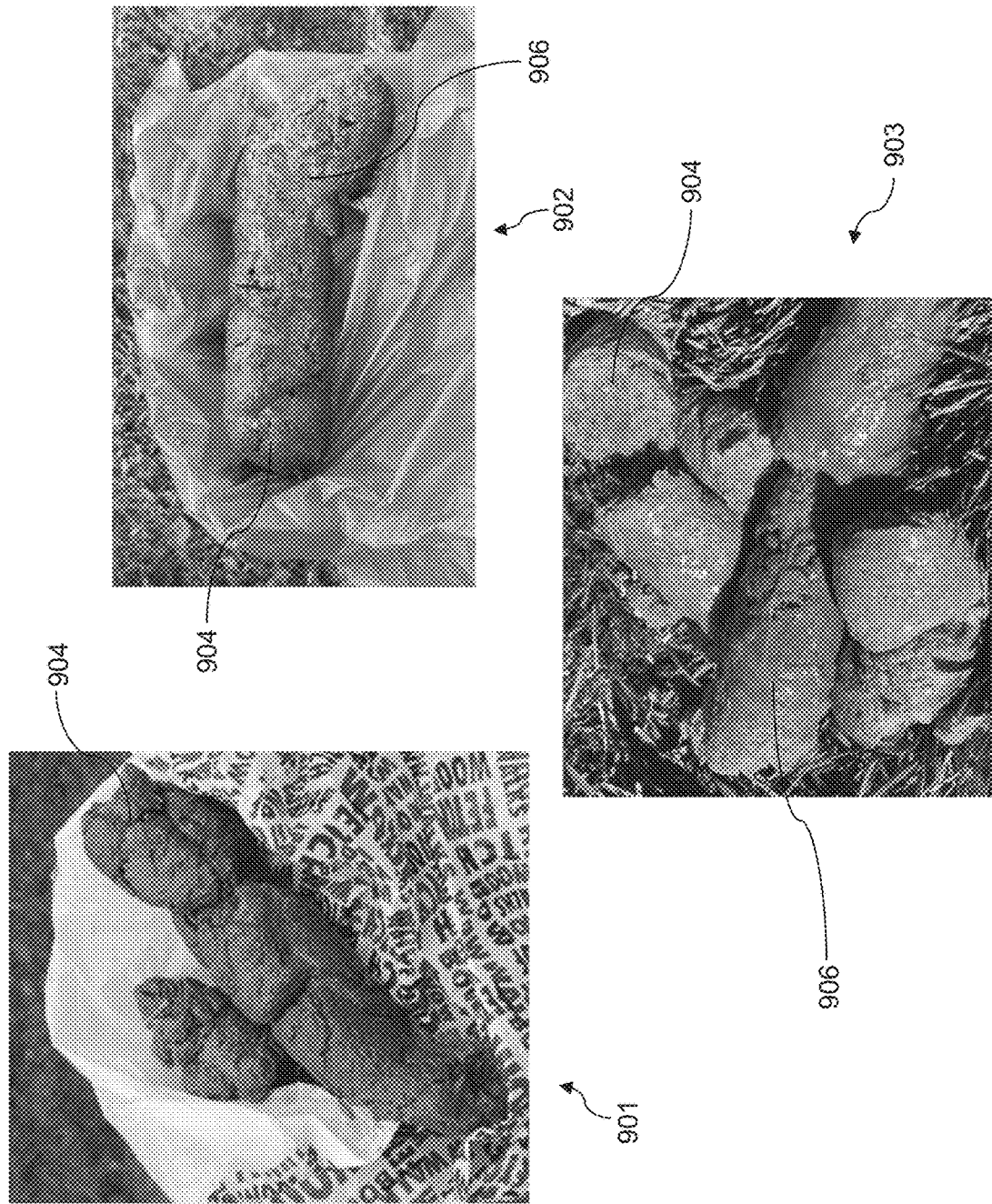
FIG. 9 shows images of biological samples to demonstrate a mucus scale, in accordance with a representative embodiment.

FIG. 9 shows images of biological samples to demonstrate a mucus scale, in accordance with a representative embodiment. Specifically, the figure includes a first image 901, a second image 902, and a third image 903, where each image contains a biological sample in the form of stool 904. As described herein, although the biological samples in these images are stool samples, other forms of biological samples are also or instead possible. These images are provided by way of example to demonstrate how a mucus scale can be created and used according to an aspect of the present teachings. And, although described here in the context of mucus, it will be understood that these techniques can be applied to the creation and use of scales for other substances and substrates besides mucus, such as any of those referenced herein.

The first image 901 shows stool 904 that is substantially absent any mucus. In this manner, a grade corresponding to an amount of mucus present for the biological sample shown in the first image 901 may be 'absent' or the like. That is, if the first image 901 is used as input for a mucus model as described herein, an output of the model may include at least a grade of 'absent' corresponding to an amount of mucus present within the biological sample. Further, if the first image 901 and/or a plurality of similar images without any mucus are used to train a model as described herein, the model may be programmed to identify the lack of mucus presence when applied to analyze images of biological samples.

The second image 902 shows stool 904 that contains some mucus 906 on the stool 904 within the image. Because the mucus 906 represents a relatively thin translucent coating and/or because the mucus 906 is on less than about half of the exudate (i.e., the stool 904), a grade corresponding to an amount of mucus 906 present for the biological sample shown in the second image 902 may be 'low' or the like. That is, if the second image 902 is used as input for a mucus model as described herein, an output of the model may include at least a grade of 'low' corresponding to an amount of mucus 906 present within the biological sample. Further, if the second image 902 and/or a plurality of similar images with some mucus 906 are used to train a model as described herein, the model may be programmed to identify the mucus 906 when applied to analyze images of biological samples and to label or grade an image accordingly.

The third image 902 shows stool 904 that contains a plethora of mucus 906 on the stool 904 within the image. Because the mucus 906 represents a relatively thick opaque coating on more than about 25% of the exudate (i.e., the stool 904), a grade corresponding to an amount of mucus 906 present for the biological sample shown in the second image 902 may be 'high' or the like. That is, if the third image 903 is used as input for a mucus model as described herein, an output of the model may include at least a grade of 'high' corresponding to an amount of mucus 906 present within the biological sample. Further, if the third image 903 and/or a plurality of similar images with a relatively large amount of mucus 906 are used to train a model as described herein, the model may be programmed to identify the mucus 906 when applied to analyze images of biological samples and to label or grade an image accordingly.

Although the example mucus scale provided herein may seem relatively simplistic (i.e., a scale of absent, low, and high), the ability to detect mucus 906 presence in a biological sample for insights into health and well-being can be quite challenging, and similarly, training a model to detect mucus content and output a grade on a mucus scale is also quite challenging. This is because, as described herein, mucus 906 is a notoriously transient and tricky substance to characterize—primarily due to its fleeting properties. For example, it is virtually impossible to preserve a mucus sample long enough to get it to a laboratory for any sort of assessment. This creates a need to better understand mucus 906 (including creating a mucus scale that is usable by a model for analyzing images of biological samples), to determine one or more health characteristics related thereto, and to formulate a health plan for an animal at least in part based on one or more of these health characteristics.

It will be understood that the mucus 906 in FIG. 9, and the discussion of mucus generally herein, mostly refers to colonic mucus, which is characterized by a distinct stratified inner layer and a less defined outer layer. Per the latest state of the art, the outer layer is often difficult to observe in colonic tissue sections or by other imaging techniques (see, e.g., Schroeder, *Gastroenterology Report*, 7(1), 2019-3-12). Mucus production is stimulated then produced and secreted by goblet cells. Inflammasome components have been suggested to be involved in controlling mucus release from goblet cells (see Johansson & Hansson, *Nat Rev Immunol.* 2016 October; 16(10):639-649). Interestingly, mucus 906 is secreted in the small intestine and travels distally along the gastrointestinal tract. The large intestine also produces mucins, which form a well-organized inner mucus structure. The inner mucus layer is constantly renewing, e.g., about every hour in laboratory mice. Endogenous proteases convert the inner layer to a detached, less dense outer later, that follows the fecal stream. Since the mucus 906 provides a semi-permeable and sometimes impermeable layer, it can be thought of as the first line of immune defense for the gut epithelium. Bacteria have also been shown to be responsible for affecting the mucosal structure and function.

While having movable mucus 906 is a vital step in maintaining small intestine homeostasis, the presence of excess mucus 906 in stool 904 is often a clue of digestive distress—e.g., a signal that the body is producing an excess of mucus 906 as an immune response to a pathogen or some other foreign intruder. Thus, an aspect of the present teachings involves the creation of a novel mucus scale to characterize the mucus 906 that is present on stool 904 (or other substrates), the determination of a health characteristic thereof, and the formulation of a health plan at least in part based on the health characteristic.

An example of how a mucus scale can be created will now be described, but it will be understood that other techniques are possible and can be utilized with aspects of the present teachings. Development of a mucus scale may include the collection of a plurality of images of biological samples and associated metadata, where the images generally include varying amounts of mucus present—e.g., from none to a relatively large amount. The images may represent a wide, dynamic range of mucus volume and conditions under which mucus 906 is present. By way of example, mucus 906 may or may not accompany diarrhea, a diet change, an external stressor such as a trauma event (e.g., moving an animal to a new location), the presence of intestinal parasites, and so on. Based on the images and metadata, a subjective scale may be created to grade the presences of mucus 906. As described above, the mucus scale may include grades such as: (i) absent (e.g., where mucus is undetected, and/or where only a trace amount of mucus is detected), (ii) low (e.g., a thin translucent coating and/or mucus 906 on less than about half of the biological sample), and (iii) high (e.g., a thick opaque coating on more than about 25% of the biological sample). Other scales are also or instead possible as will be understood by a skilled artisan.

The biological samples contained in the plurality of images may then be classified according to the aforementioned mucus scale. In this manner, a predictive computer vision model may be programmed to self-classify biological samples within images into these grades when a new, non-trained image is presented to the model.

It will be understood that the grades of the exemplary mucus scale can be directly associated with the amount of digestive distress an animal is experiencing, and in this manner, the grades can be used to predict a health characteristic of an animal from which the mucus originated. Furthermore, the opacity and physical regularity of the mucus 906 can be an additional or alternative condition used to build incremental models, to make health characteristic predictions, and to formulate treatments for animals.

Figure 10:
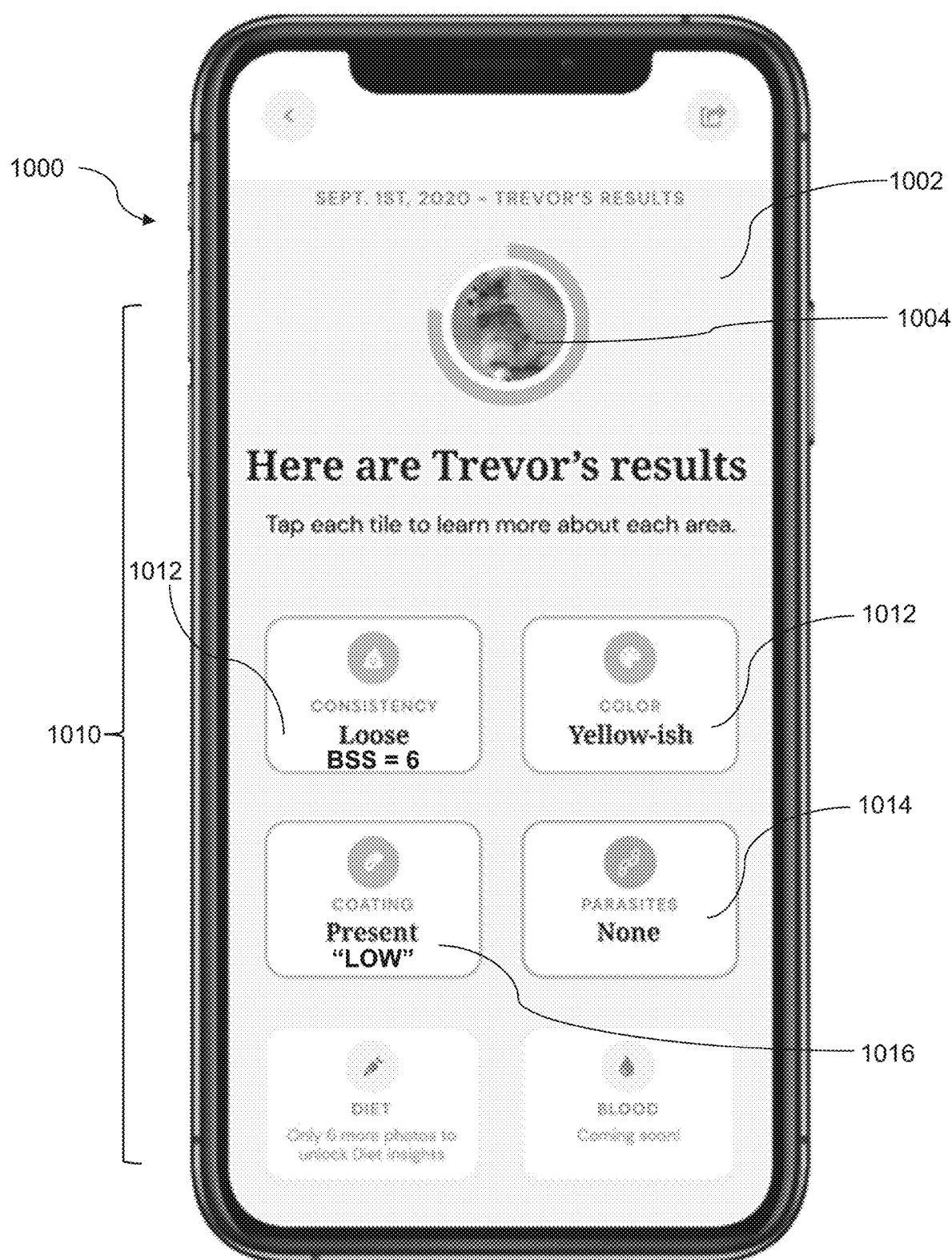
FIG. 10 shows output of an image analysis of a biological sample presented to an end user, in accordance with a representative embodiment.
Figure 11:
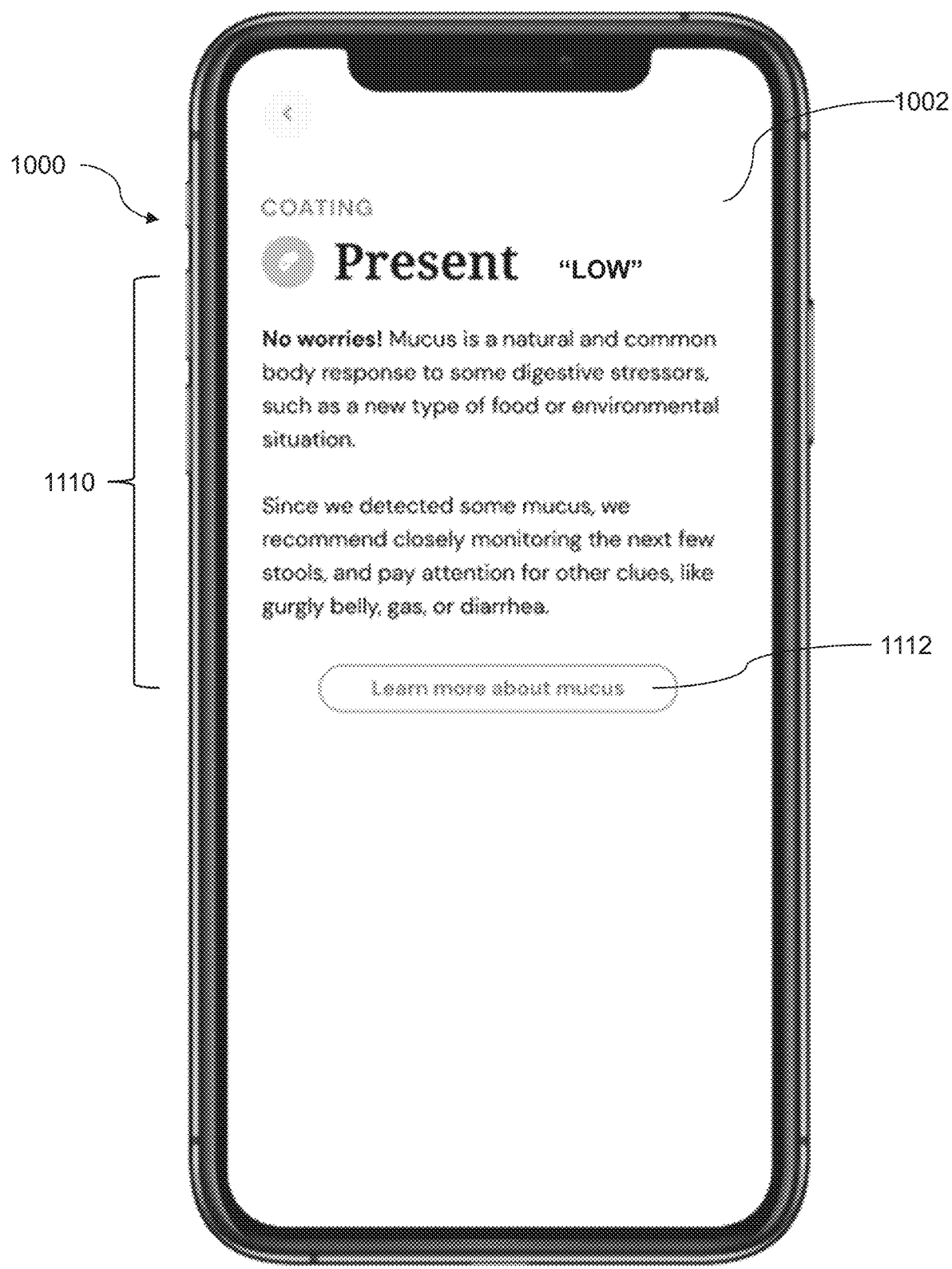
FIG. 11 shows a grade relating to a mucus scale, in accordance with a representative embodiment.
Figure 12:
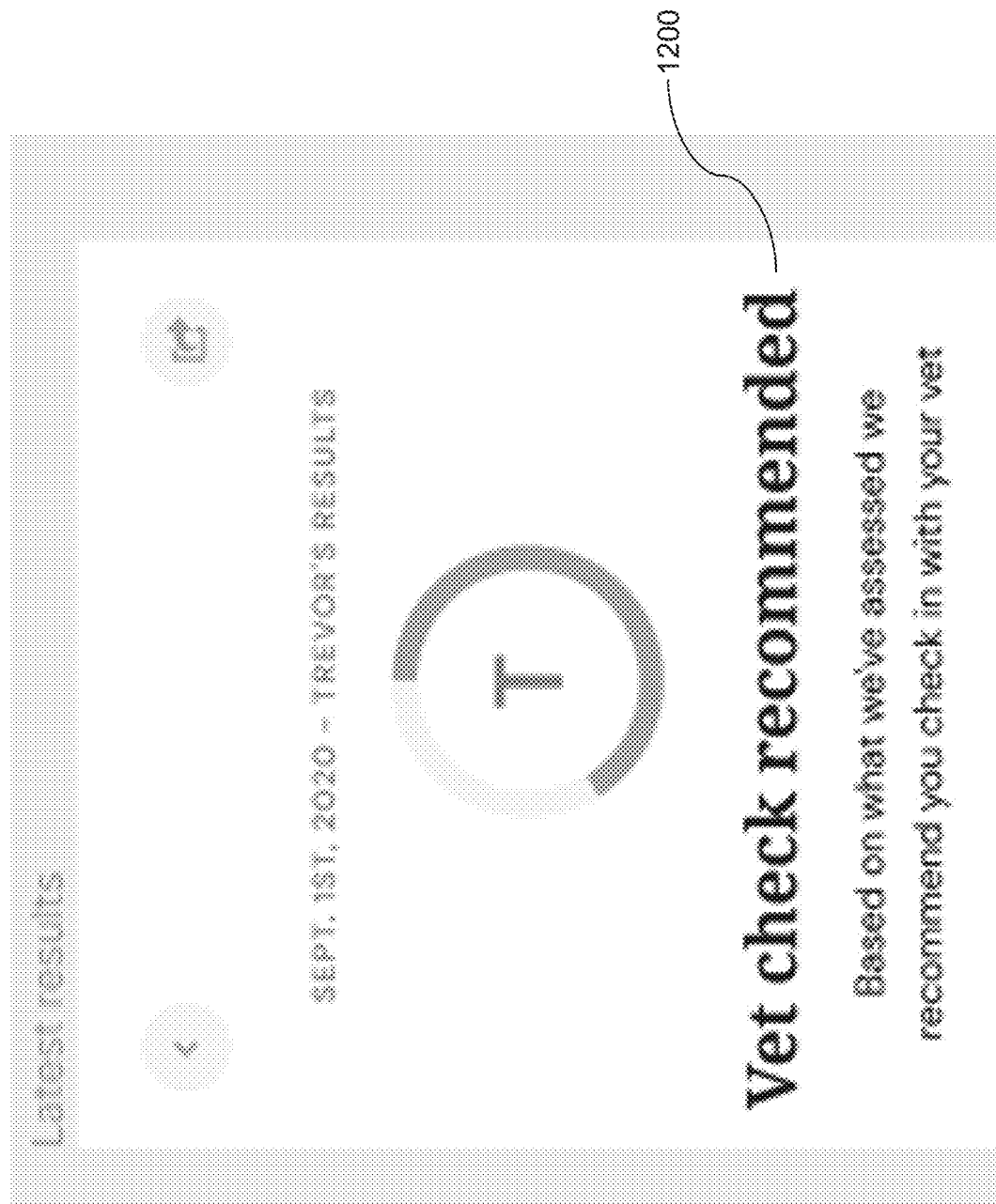
FIG. 12 shows a treatment recommendation, in accordance with a representative embodiment.

Thus, as described herein, certain aspects of the present teachings involve an end user taking a photograph of a biological specimen and submitting (e.g., uploading) the resulting digital image of the biological specimen for image analysis in order to receive a health characteristic for an animal from which the biological specimen was derived based on the image analysis. And, in certain aspects, one or more of the aforementioned steps is accomplished using a smartphone or similar end user computing device (e.g., all of the aforementioned may be done on a smartphone, and/or utilizing a backend resource in communication with the smartphone such as a remote computing resource through a web-based application). By way of example, a user may be a pet owner, where functionality of much of the present teachings is accessible to the user via a mobile application disposed on a user's computing device such as their smartphone. In this manner, the user can take a photograph of their pet's stool using their smartphone, upload the resulting image for analysis (e.g., using a mobile application), and receive a health characteristic or other data that is part of output resulting from an image analysis of the image of their pet's stool. FIGS. 10-12 show examples of such output that can be presented to a user from an image analysis of a biological sample in the form of stool.

FIG. 10 shows output of an image analysis of a biological sample presented to an end user, in accordance with a representative embodiment. In particular, this figure shows output 1010 of an image analysis of a biological sample presented on a display 1002 of a computing device 1000, which may be a smartphone associated with a user in the example provided above. The display 1002 may be an interactive graphical user interface, such as a touchscreen or the like, such that the user can interact with the output 1010 or other information presented to the user on the display 1002.

In this example, the user's pet is a dog named "Trevor," i.e., the animal 1004 associated with the biological specimen in the image that was analyzed to generate the output 1010 shown. And in this example, the biological specimen is stool, although other forms of biological specimens are also or instead possible as described herein. The state of the display 1002 in FIG. 10 may represent a screen that is presented after the user has submitted a digital photograph that has been analyzed—locally, using processing capabilities of the user's device, or remotely, using a backend computing resource in communication with the user's device, or a combination thereof—according to an aspect of the present teachings. It will be understood that the example here in FIG. 10 is independent from the examples provided for context with reference to FIG. 9.

Turning back to FIG. 10, as shown in the figure, the output 1010 may include one or more labels 1012 corresponding to a feature of the biological specimen identified in the image analysis, as well as one or more health characteristics 1014, and one or more grades 1016 corresponding to an amount of mucus present in at least a portion of the biological specimen.

In this example, the labels 1012 include a consistency of the biological specimen and a color of the biological specimen—where, more particularly, the stool sample in this example had a "loose" consistency and a "yellow-ish" color. And, by way of example, further information may be provided with the labels 1012. For example, a label 1012 associated with consistency may further include a Bristol Stool Score (BSS), e.g., where a BSS of 6 is provided by way of example in the figure. It will be understood that such further information (like a BSS) can instead be provided as a health characteristic 1014 as that term is defined herein—i.e., where this information is derived from an image analysis and its output 1010, such as a collective analysis of labels

1012 for consistency and color, or other data. It will also be understood that more or less labels 1012 are possible. For example, output 1010 of the image analysis (e.g., a model such as a CNN model that performs all or part of the image analysis) may also or instead include labels 1012 corresponding to one or more of an opacity of the biological specimen or a portion thereof (e.g., mucus present in the biological specimen), a thickness of the biological specimen or a portion thereof (e.g., mucus present in the biological specimen), a surface area occupied by mucus or another substance, a color of mucus present in the biological specimen, an estimate of microbial content of the biological specimen or a portion thereof (e.g., mucus present in the biological specimen), an estimate of a level of cortisol in the host animal, an estimate of a level of bacteria in the biological specimen or a portion thereof (e.g., mucus present in the biological specimen), detection of blood, detection of a pathogen, and the like. In general, the labels 1012 shall be understood to include an image feature or characteristic that is identified (and in some instances quantified, or that otherwise may include derived information therefrom) as part of an image analysis as described herein.

A health characteristic 1014 may generally include information derived from an image analysis and its output 1010. For example, a health characteristic 1014 may include a prediction based on output 1010 of a model that performs at least some of the image analysis. Thus, in general, the labels 1012 may include identified features or characteristics of a biological specimen, and the health characteristics 1014 may include derived information related to a label 1012 or another form of output 1010 from an image analysis. It will be understood that, in some instances, there may be overlap between labels 1012 and health characteristics 1014 as defined herein, and this example demonstrates one such instance. Specifically, in this example, the health characteristic 1014 includes that no parasites were detected in the stool sample. It will be understood, however, that this particular health characteristic 1014 could also or instead be a label 1012. That is, it may be directly observable (e.g., by the model) that no parasites are located in the stool sample (in which case it would be a label 1012 as defined herein) and/or the lack of parasites may be derived from other data that is identified or discerned from an image analysis (in which case it would be a health characteristic 1014 as defined herein) such as a relatively healthy-looking stool sample.

In this example, the grade 1016 corresponds to an amount of mucus present in a biological specimen, although other grades are certainly possible. A grade 1016 in this context may simply be thought of as a label 1012, a health characteristic 1014, or the like that can be placed on a particular scale—e.g., the mucus scale as described herein, which may identify the amount of mucus as one of absent, low, or high. In this example, the grade 1016 is "low" and it corresponds to mucus presence—i.e., there is only a relatively small amount of mucus contained in the stool sample image used in this example. A grade 1016 (and/or a label 1012, a health characteristic 1014, or the like) may also or instead include a color score, an opacity score, identification of the microbial content of the biological specimen, and the like, which can be useful for providing more precise health planning and recommendations.

As stated above, the display 1002 may be an interactive graphical user interface. In this manner, a user may be provided an opportunity to select one or more of the outputs 1010 or other information on the display 1002 to access additional or different information. An example of selecting the grade 1016 corresponding to the amount of mucus present is shown in FIG. 11.

FIG. 11 shows a grade relating to a mucus scale, in accordance with a representative embodiment. Similar to FIG. 10 and continuing with the example above, FIG. 11 shows a display 1002 of a computing device 1000, which may be a smartphone as stated above. In particular, the display 1002 of FIG. 11 may include information 1110 that is shown when a user selects one or more of the outputs 1010 of FIG. 10, and specifically the grade 1016 of FIG. 10. Thus, in this example, the information 1110 is related to a grade 1016 of "low" on a mucus scale, and may thus include a descriptor of the grade 1016. As such, the exemplary information 1110 states "No worries! Mucus is a natural and common body response to some digestive stressors, such as a new type of food or environmental situation. Since we detected some mucus, we recommend closely monitoring the next few stools, and pay attention for other clues, like gurgly belly, gas, or diarrhea." Other information 1110 is also or instead possible. For example, the information 1110 displayed here may include one or more of a treatment for the animal (e.g., a customized health plan as described herein, and/or a food, supplement, or medicine recommendation or prescription), other descriptors, a report, a warning, an alert, the image, and the like.

Moreover, the display 1002 may include one or more selections 1112, which may include hyperlinks or the like to other information and the like. This other information may be stored locally, remotely, and/or may be derived from third-party platforms, websites, applications, and the like. For example, the selection 1112 in the example of FIG. 11 may direct a user to a veterinary health website or the like.

FIG. 12 shows a treatment recommendation, in accordance with a representative embodiment. Similar to the examples shown in FIGS. 10-11, a treatment 1200 may be provided to a user on a display of a computing device. In this example, the treatment 1200 includes a recommendation to see a veterinarian for an animal associated with a biological sample based on an image-based analysis of the biological sample. The treatment 1200 may be accessible via a selection in one or more of the displays described above or similar, and/or the treatment 1200 may be transmitted via a report, a push notification, a text message, an electronic mail message, and the like.

Thus, as generally described above with reference to FIGS. 10-12, based on the mucus scale and/or other classifications created and applied to an image analysis, one or more of grades, health attributes, and labels may be provided to a user, along with other helpful information such as one or more descriptors of the foregoing as well as a treatment and/or recommendation (e.g., a determination of whether or not to seek veterinary care). In this manner, based on mucus and/or other attributes of a biological sample (such as consistency, color, and presence of parasites), a health plan can be formed that may include dietary, medication, and/or a personalized supplement. For example, with a high mucus classification, a recommendation may be made for the addition of one or more of slippery elm bark powder and marshmallow root powder in a dog's supplement, which can support mucus health. Probiotics could also be added to support gastrointestinal health. Other health plans and treatments are also or instead possible.

Figure 13:
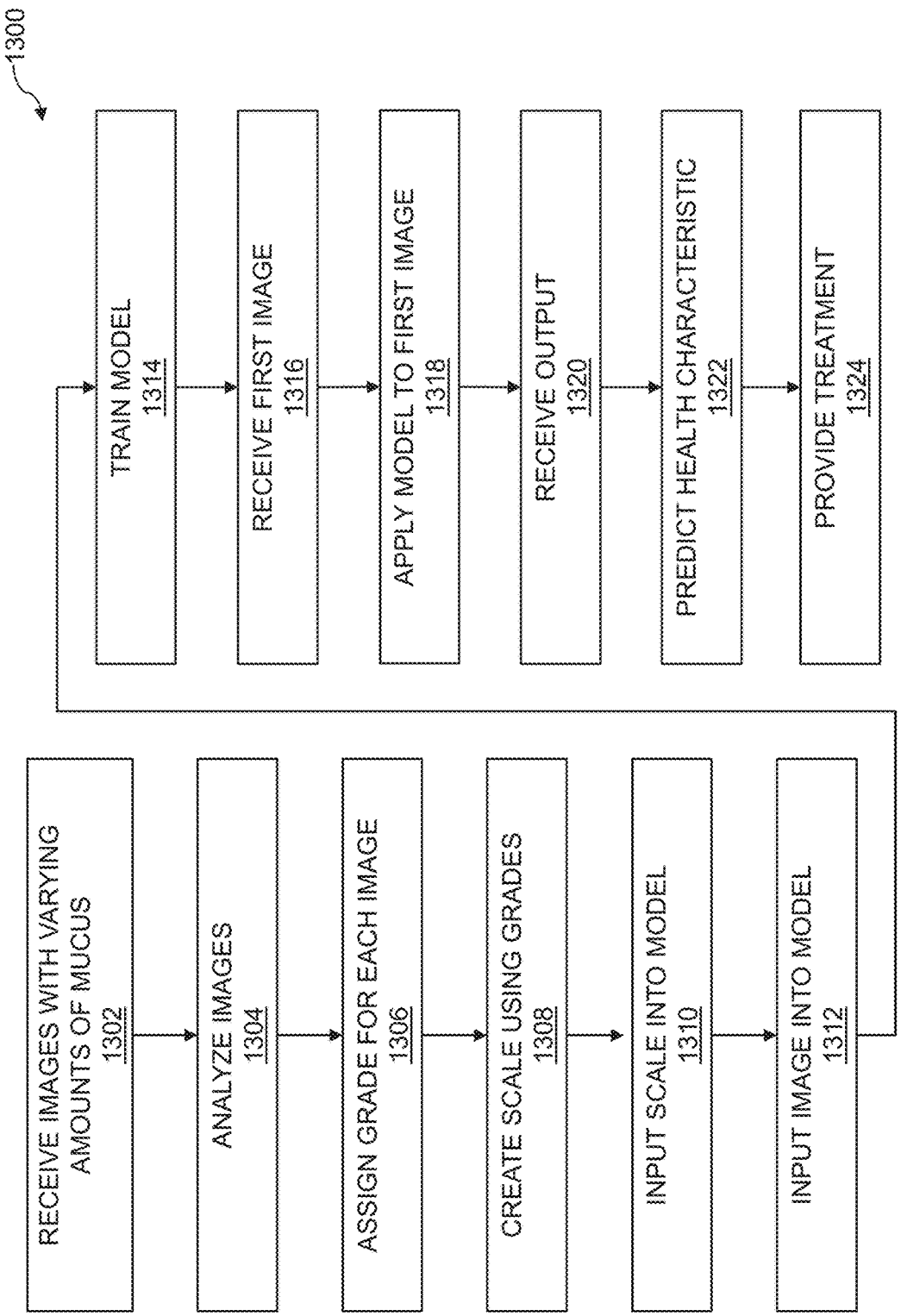
FIG. 13 is a flow chart of a method of creating and using a mucus scale, in accordance with a representative embodiment.

FIG. 13 is a flow chart of a method of creating and using a mucus scale, in accordance with a representative embodiment. The method 1300 may include the creation and use of a mucus scale as described herein such as with reference to FIGS. 9-12 above—e.g., a mucus scale related to an amount of mucus present in a biological sample such as a stool sample. The scale created according to the method 1300 may be specifically tailored for use in an image-based analysis of biological samples, where a mucus analysis of such samples in the prior art was challenging or impossible. This is because, as explained herein, mucus is a notoriously transient and challenging substance to characterize due to its fleeting properties. Therefore, the ability to detect mucus presence in a biological sample for insights into health and well-being can be quite challenging, and similarly, training a model to detect mucus content and output a grade on a mucus scale (among other output) can also be quite challenging. However, using techniques of the present teachings, such as the method 1300 of FIG. 13, a mucus scale can be created that is usable by a model for analyzing images of biological samples to determine one or more health characteristics related thereto, and to formulate a health plan for an animal at least in part based on one or more of these health characteristics. And, as described herein, the use of such a scale and model can be implemented using a mobile application or the like, thereby allowing a user to take a photo of a biological sample, upload the photo through such a mobile application for analysis, and receive useful feedback based on an image analysis of the photo, such as a grade on a mucus scale, a prediction related to health, and/or a treatment.

As shown in step 1302, the method 1300 may include receiving a plurality of images of biological samples containing varying amounts of mucus. The images may be garnered specifically for the purpose of creating a mucus scale, and/or some of the images may be existing images of biological samples containing varying amounts of mucus. The plurality of images may include, for example, hundreds or thousands of images. As explained herein, the biological samples in the plurality of images may each include a stool sample, although other forms of biological samples are also or instead possible as explained herein. The varying amounts of mucus in the plurality of images may range from an absence of mucus to a relatively large amount of mucus. In some implementations, a "large" amount of mucus may be defined by an occupation of more than 25 percent of a biological sample. Other factors may also or instead define a range for mucus content, and/or be used for other mucus-related properties.

As shown in step 1304, the method 1300 may include analyzing the plurality of images of biological samples. The analysis may be automated (e.g., computer implemented), manual (e.g., using a human reviewer), or a combination thereof. The analysis may include reviewing the images to identify whether mucus is present, and if so, identifying a quantity (or other property) thereof.

As shown in step 1306, the method 1300 may include assigning, for each of the plurality of images, one of a number of grades associated with an amount of mucus present on biological samples contained therein. In certain aspects, the number of grades correspond to at least a first condition where mucus is undetected from a biological sample in at least one of the plurality of images, a second condition where mucus is detected but occupies less than a predetermined amount of a biological sample in at least one of the plurality of images, and a third condition having mucus that occupies more than the predetermined amount of a biological sample in at least one of the plurality of images. As explained herein, the first condition may include a grade of 'absent,' the second condition may include a grade of 'low,' and the third condition may include a grade of 'high.' Other conditions and/or grades are also or instead possible, such as more than three conditions, which will be understood to be a useful example for understanding the present teachings.

By way of example, the predetermined amount that distinguishes one grade from another (e.g., 'low' to 'high') may be a coating of 25 percent of the biological sample. In other aspects, the predetermined amount may be a coating of 50 percent of the biological sample. Other amounts are possible as will be understood by a skilled artisan.

It will further be understood that, instead of or in addition to a grade corresponding to an amount of mucus present in an image of a biological sample, grades corresponding to other properties of mucus are possible. For example, a grade in the number of grades may account for one or more of: an opacity of mucus, a thickness of mucus, a surface area occupied by mucus, a color of mucus, an estimate of microbial content of mucus, an estimate of a level of cortisol in an animal associated with the biological sample, an estimate of a level of bacteria in mucus, and so on.

As shown in step 1308, the method 1300 may include creating a scale that includes each grade of the number of grades. Thus, using the example provided herein, the scale may include grades of 'absent,' 'low,' and 'high.'

As shown in step 1310, the method 1300 may include inputting the scale into a model programmed to perform an image analysis on an input image, where an output of the model in the image analysis may include one of the number of grades. Stated otherwise, this step 1310 may include programming a model to analyze images of biological samples with respect to mucus by learning from grades assigned to known images.

As shown in step 1312, the method 1300 may include inputting the input image into the model, and receiving the output including one of the number of grades for the input image. An expected output for the model from analyzing the input image may be known. In this manner, and as shown in step 1314, the method 1300 may include training the model by reviewing the output and adjusting the model when the output does not match an expected output. By way of example, the input image may contain a relatively large amount of mucus, and thus, if the output of the model diverges from an identification and grade that reflects the relatively large amount of mucus present in the input image, the model may be adjusted.

The method 1300 may further include the use of the scales in an image-based analysis as described herein. In this manner, and as shown in step 1316, the method 1300 may include receiving a first image including a first biological sample, and identifying and extracting one or more regions of interest within the first image for further analysis.

As shown in step 1318, the method 1300 may include applying the model to one or more regions of interest within the first image to identify one or more conditions of mucus therein. The model may be the same model that was trained above using the mucus scale, and thus a condition of mucus identified by the model may include an amount of mucus present within the first image and the biological sample contained therein.

As shown in step 1320, the method 1300 may include receiving output of the model for the first image. The output may include at least a first grade of the number of grades— by way of example, a grade of 'absent,' 'low,' or 'high.'

As shown in step 1322, the method 1300 may include, based at least in part on the first grade, predicting a health characteristic of an animal from which the first biological sample originated. The health characteristic may be any one or more of the health characteristics described herein. Further, the method 1300 may include presenting the health characteristic to a user associated with the animal—e.g., via transmitting the health characteristic to a computing device associated with the user.

As shown in step 1324, the method 1300 may include providing a treatment for the animal in view of one or more of the health characteristic and the first grade. The treatment may be any one or more of the treatments described herein.

FIG. 14 shows an image and various color planes thereof, in accordance with a representative embodiment. Specifically, FIG. 14 includes an image 1400 featuring a resting surface 1410 that may be structurally configured for use in image analysis of a biological sample (e.g., a mucus sample contained on stool) that is at least partially disposed thereon. To that end, the resting surface 1410 may include one or more predetermined markings thereon as described herein, e.g., where such markings may be used for extracting one or more of the color attribute and the dimensional attribute as described herein. By way of example, the figure shows normalization of example color planes using the predetermined markings of the resting surface 1410—i.e., the red color plane 1412, the green color plane 1414, and the blue color plane 1416.

FIG. 15 shows examples of segmentation of images of stool samples for a mucus analysis, in accordance with a representative embodiment. Specifically, FIG. 15 includes examples of segmentations of the images included in FIG. 9 described above. As shown in FIG. 15, after a segmentation operation, an image featuring a biological sample in the form of a mucus sample disposed on a stool substrate may be segmented to remove one or more of portions of a resting surface or other background portions, as well as portions of the stool sample itself that may not be pertinent for an image analysis of mucus contained thereon. The segmentation may include a first segmentation of the image, which substantially isolates the mucus plus stool substrate sample. The segmentation may also include a second segmentation of the image that isolates just the resting surface, which can be used for further processing (e.g., for calculating aspect ratios, for image normalization, and so on). It will be understood, however, that such a second segmentation may not be necessary.

As described herein, the present teachings may include feature extraction from an image of a biological sample. From a high level, features may be extracted mathematically from the input images. For example, for the geometry attribute(s), the input image may be binarized, where pixel distances are calculated from various properties. By way of example, for major/minor ratio, the center of the eclipse may be calculated, and then the distance from the center to the corresponding point may be calculated. These units may be in pixels, which is why the aspect ratio may be used to convert back to another form such as inches or millimeters.

Figure 16:
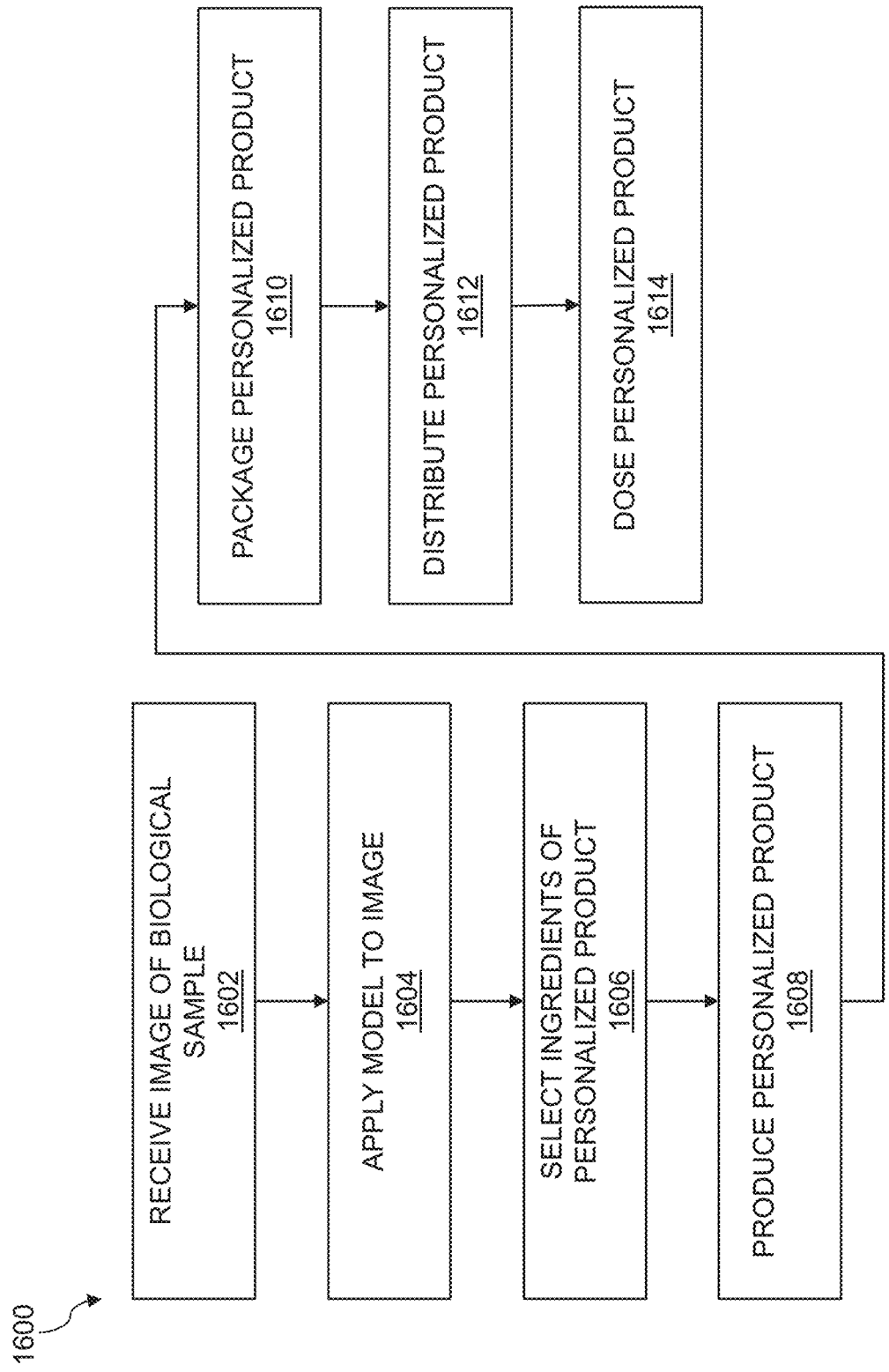
FIG. 16 is a flow chart of a method of formulating a personalized product for an animal.

FIG. 16 is a flow chart of a method of formulating a personalized product for an animal. It will be understood that the method 1600, similar to the other methods shown and described herein, may be combined with, supplemented to, and/or substituted for any of the other techniques described herein. In this manner, it will be understood that the method 1600 of formulating a personalized product for an animal may include use of an image analysis of a biological sample, e.g., where such an image analysis forms the entire basis for the formulation of the personalized product.

The personalized product may include a personalized dietary product. The personalized dietary product may include one or more of a food, a supplement, a medicine, and the like. To this end, the personalized dietary product may include a predetermined amount of one or more of a probiotic, a prebiotic, a digestive enzyme, an anti-inflammatory, a natural extract, a vitamin, a mineral, an amino acid, a short-chain fatty acid, an oil, a formulating agent, and the like. The personalized product including a personalized dietary product may be advantageously created based on analysis of a biological sample in the form of a mucus sample or the like, e.g., contained within an image of stool. Also, or instead, the personalized product may be created based on analysis of a biological sample in accordance with the present teachings combined with an analysis according to the teachings of Int'l Pat. App. No. PCT/US20/44507 filed on Jul. 31, 2020, which is incorporated by reference herein in its entirety.

The personalized product may also or instead include a non-dietary product. For example, the personalized product may include one or more of a grooming product, a shampoo, a conditioner, a lotion, a cream, a medicine, an ear drop, an eye drop, a topical substance, a toothpaste, an oral rinse, a chew (e.g., a chew toy or the like that can be provided for health benefits such as oral hygiene), and the like.

As shown in step 1602, the method 1600 may include receiving an image including a biological sample therein, e.g., a stool sample containing mucus or the like.

As shown in step 1604, the method 1600 may include applying a model to the image to extract one or more features of the biological sample. The model may be any as described herein, and the extraction of the features of the biological sample may utilize any of the image analysis techniques described herein.

As shown in step 1606, the method 1600 may include, based at least on one or more features of the biological sample extracted from the model, selecting one or more ingredients of a personalized product for an animal from which the biological sample originated. Thus, the method 1600 may include creating a unique formula for the personalized product by selecting one or more ingredients and use levels for an animal from which the biological sample originated. In this manner, it will be understood that the personalized product may include a personalized formula.

As shown in step 1608, the method 1600 may include producing the personalized product, which may include combining the one or more ingredients (e.g., at custom use levels) to form the personalized product, e.g., to produce a personalized formula. For example, this may include combining all of the ingredients into a single product (e.g., where the ingredients form one or more of a powder, a pill, a paste, a liquid, a solid, and so on). This may also or instead include combining the ingredients into a single container or housing, e.g., for shipping and/or transport, but where individual ingredients may be separated from one another, which can be advantageous for particular dosing schemes.

As shown in step 1610, the method 1600 may include packaging the personalized product, e.g., for distribution such as shipping to a user. Stated otherwise, this may include packaging a personalized formula, e.g., for distribution such as shipping to a user, thereby comprising a personalized product.

As shown in step 1612, the method 1600 may include distributing the personalized product to one or more of the animal and a user associated with the animal (e.g., an owner of the animal, a veterinarian, a physician, and so on).

As shown in step 1614, the method 1600 may include dosing the personalized product for the animal. This may include separating particular doses of the personalized product for ease of use by an end-user. This may also or instead include providing a dosing component such as a scoop, a spoon, a vial, a measuring cup, a syringe, a packet (e.g., a blister pack, foil, etc.), and so on, in conjunction with providing the personalized product. The dosing method may also or instead include a personalized dosing component to assist in ensuring accurate administration of the personalized product. It will be understood that the personalized dosing component may be custom-tailored for a specific animal or set of animals.

Several other aspects of the present teachings are described below by way of example.

Data Wrangling and Preparation of Data

Mucus Health Features:

Data may be extracted from source, e.g., a database such as a remote, cloud-based database. Images may be the data used for the model. Every image may be labeled with corresponding mucus levels associated with an amount of mucus present. The mucus levels used may be high, low, and none (or similar)—although it will be understood that other labels (included more detailed amounts) can be used. Continuing with this example, however, every image may be labeled with one of these three labels, where the labels are converted into numerical values. By way of example, 0 may correspond to high, 1 may correspond to low, and 2 may correspond to none. Other numerical values may be possible as will be understood by a skilled artisan. Every image may be resized, converted to a tensor, and fed into the CNN with its corresponding label.

Thus, stated otherwise, data may be extracted from a source, such as a spreadsheet and/or a relational/non-relational database stored locally or on the cloud. Data may be loaded into software, such as a high-level, general-purpose programming language. Data may be transformed as needed (e.g., scaling data to unit mean and variance). Data can continue to be cleaned prior to analysis (e.g., string formatting, removing null values, converting object types). Feature matrix X may be formatted and vector y may be labeled. Feature matrix X can have any number of attributes and/or features, including geometric attributes, color attributes, and so on. Feature vector y may contain a true class label such as a mucus health score. Additionally, data may include laboratory data such as cortisol levels of a host animal, bacteria counts, and the like.

Semantic Segmentation:

Images and corresponding ground truth labels may be stored in a data source (e.g., local and/or cloud). Images may be extracted from a source (e.g., local and/or cloud based storage). Images may be resized to standard or otherwise predetermined sizes. Images may be augmented (e.g., cropping, flipping vertically/horizontally, shearing, rotating, etc.) to increase dataset size to both raw and ground truth. It will be understood that these steps may be automated with software.

Modeling

Mucus Health Features:

The dataset be split into training, testing, and/or validation sets, using a portion of data (e.g., about 70%-80%) to train the model, where some data (e.g., about 20%-30%) is reserved to test the data after training, and for validating (e.g., about 10%) the model during training. The model may then be created, e.g., from loading from a package or a defined architecture. The model may be trained using training data, where validation data is optionally fed-in to validate during training. Model accuracy may be evaluated with testing data, e.g., comparing predictions to ground truth. Model hyperparameters can be optimized using routines such as cross-validation, grid search, and the like to propose parameters that can lead to desired accuracy, bias, and/or variance. The model may be saved to be called at runtime, where the model may have an API to be called programmatically at runtime. It will be understood that these steps may be automated with software.

Semantic Segmentation:

A custom convolutional neural network (CNN) architecture or instantiate CNN architecture that is known (e.g., U-Net) may be defined. The dataset be split into training, testing, and/or validation sets, using a portion of data (e.g., about 70%-80%) to train the model, where some data (e.g., about 20%-30%) is reserved to test the data after training, and for validating (e.g., about 10%) the model during training. The model may be trained using training data, where validation data is optionally fed-in to validate during training. Model accuracy may be evaluated with testing data, e.g., comparing predictions to ground truth (e.g., DICE coefficients). Model hyperparameters can be optimized using routines such as cross-validation, grid search, and the like to propose parameters that can lead to desired accuracy, bias, and/or variance. The model may be saved to be called at runtime, where the model may have an API to be called programmatically at runtime.

Mucus:

A pre-trained, open source, model (e.g., ResNet, which was previously trained on an ImageNet dataset of several million images) may be loaded. This model may be fine-tuned by modifying the architecture of the model by changing the last layers to match as per the needs of the objective function. The image dataset may be split into train and validation sets in the ratio of 80-20 or similar. The images may be sent to the model with their corresponding labels (e.g., none, low, and high) while training. The training may be performed on a graphics processing unit (GPU). Pre-trained, open source, model weights (e.g., ResNet, which was previously trained on several million images) may be loaded. The weights may then be adapted as desired for the operation of the present teachings. Image class metadata may be passed in, which for example can be organized by folder name and/or passed as a dictionary/list object with corresponding class names per image. The train test may be split, using a portion of data (e.g., about 70%-80%) to train the model, where some data (e.g., about 20%-30%) is reserved to test the data after training, and for validating (e.g., about 10%) the model during training. The model may be trained using training data, where validation data is optionally fed-in to validate during training. Model accuracy may be evaluated with testing data, e.g., comparing predictions to ground truth (e.g., DICE coefficients). Model hyperparameters can be optimized using routines such as cross-validation, grid search, and the like to propose parameters that can lead to desired accuracy, bias, and/or variance. The model may be saved to be called at runtime, where the model may have an API to be called programmatically at runtime.

Code Example

It will be understood that particular portions of the disclosed techniques for analyzing an image of a biological sample image to provide a health assessment of an animal associated therewith may utilize preexisting algorithms and/or models that can be adapted to perform the particular portions.

In this example, first, the Pytorch library, Pytorch Transforms, and pre-trained models may be imported as follows:
  import torch
  from torchvision import transforms, datasets, models
The following transformations may be applied on the data:

```
image_transforms = {
  'train': transforms.Compose(
transforms.Resize((512,512)),
transforms.ColorJitter(brightness=0.5,contrast=
0.5,saturation=0.5, hue=0.5),
transforms.RandomRotation(degrees=30),
transforms.RandomHorizontalFlip( ),
transforms.RandomVerticalFlip( ),
transforms.ToTensor( ),
    ]).
    'valid': transforms.Compose([
      transforms.Resize((512,512)),
      transforms.ToTensor( ),
```

These transformations on the dataset are shown in the below code:

```
data = {
  'train': datasets.ImageFolder(root=train_directory,
transform = image_transforms['train']),
  'valid': datasets.ImageFolder(root=valid_directory,
transform=image_transforms['valid']),
}
train data = DataLoader(data['train'],batch_size=batch, shuffle=True)
valid data = DataLoader(data['valid'], batch_size=batch, shuffle=True)
```

The structure of the data directory may be as shown below:

```
                                    /train
                                    |-high
                                    |-low
                                    |-none
                                    /valid
                                    |-high
                                    |-low
                                    |-none
```

The following snippet is an example of code for the model architecture:

```
resnet = models.resnet18(pretrained=False)
for param in resnet.parameters( ):
  param.requires_grad = False
fc_inputs = resnet.fc.in _features
resnet.fc = nn.Sequential(
  nn.Linear(fc_inputs, 256),
  nn.ReLU( ),
  nn.Dropout(0.4),
  nn.Linear (256, 3)
)
model = resnet.to(device)
```

The device used here in this example is a GPU; the loss function used is Cross Entropy; and the optimizer is Adam with the learning rate of 0.001:
  optimizer=optim.Adam(model.parameters( ), lr=0.001)
  loss criterion=nn.CrossEntropyLoss( )
The above model in this example is trained to optimize the loss function using the Adam optimizer for 100 epochs and batch size of 16.

It will be understood that the code recited herein is provided by way of example and understanding only, and that other similar code may be used. Also, it would be apparent to one skilled in the art how to practice the present teachings even without such examples of code, e.g., because of the ample disclosure provided herein regarding the functionality of the models and the like described herein. One skilled in the art will further understand that code examples provided above reference reading files from a disk, e.g., raw text files, and given the significant detail of the present teachings described herein, such files and code could be created by a skilled artisan to recreate aspects of the present teachings.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

Unless the context clearly requires otherwise, throughout the description, the words "comprise," "comprising," "include," "including," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method of analyzing an image of a biological sample to provide a health assessment of an animal, the method comprising:

receiving an image of a biological sample containing mucus from a camera of a smartphone;

identifying and extracting one or more regions of interest within the image for further analysis;

applying a model to the one or more regions of interest to identify one or more conditions of mucus therein, the model trained using a plurality of images having varying conditions of mucus, wherein output of the model includes at least a grade corresponding to an amount of mucus present in the one or more regions of interest;

based at least in part on the output of the model, predicting a health characteristic of an animal from which the biological sample originated without laboratory analysis of the biological sample; and presenting the health characteristic to a user associated with the animal.

2. The method of claim 1, further comprising providing a treatment for the animal in view of the health characteristic.

3. The method of claim 2, wherein the treatment includes a customized health plan for the animal.

4. The method of claim 3, wherein the customized health plan includes one or more of a behavioral change and a dietary change.

5. The method of claim 3, wherein the customized health plan includes a recommendation regarding one or more of diet, sleep, exercise, and an activity.

6. The method of claim 2, wherein the treatment includes one or more of a food, a supplement, and a medicine.

7. The method of claim 2, wherein the treatment includes a personalized dietary supplement for the animal.

8. The method of claim 7, wherein the personalized dietary supplement includes a predetermined amount of one or more of a probiotic, a prebiotic, a digestive enzyme, an anti-inflammatory, a natural extract, a vitamin, a mineral, an amino acid, a short-chain fatty acid, an oil, and a formulating agent.

9. The method of claim 1, further comprising providing a report for the animal that includes the health characteristic.

10. The method of claim 1, wherein a descriptor is provided to the user accompanying the health characteristic.

11. The method of claim 1, wherein an alert is provided to the user in view of the health characteristic.

12. The method of claim 1, wherein the grade identifies the amount of mucus as one of absent, low, or high.

13. The method of claim 1, wherein output of the model further includes one or more labels corresponding to at least one of: an opacity of mucus present in the one or more regions of interest, a thickness of mucus present in the one or more regions of interest, a surface area occupied by mucus in the one or more regions of interest, a color of mucus present in the one or more regions of interest, an estimate of microbial content of mucus present in the one or more regions of interest, an estimate of a level of one or more of bacteria and cortisol in the animal, and detection of one or more of blood and a pathogen.

14. The method of claim 1, wherein the model is a convolutional neural network (CNN) model.

15. The method of claim 1, wherein the biological sample includes a stool sample, the method further comprising calculating one or more of a geometric attribute, a texture attribute, and a color attribute within the one or more regions of interest to identify one or more features of the stool sample.

16. The method of claim 15, further comprising applying a second model to the one or more features of the stool sample, the second model predicting a second health characteristic of the animal based on the one or more features.

17. The method of claim 16, further comprising providing a treatment in view of a combination of the health characteristic and the second health characteristic.

18. The method of claim 1, wherein the grade corresponding to the amount of mucus present in the one or more regions of interest is based at least in part on a percentage of coverage of mucus on the one or more regions of interest as deduced by the model.

19. A computer program product for analyzing an image of a biological sample to provide a health assessment of an animal, the computer program product comprising computer executable code embodied in a non-transitory computer readable medium that, when executing on one or more computing devices, performs the steps of:
- receiving an image of a biological sample containing mucus from a camera of a smartphone;
- identifying and extracting one or more regions of interest within the image for further analysis;
- applying a model to the one or more regions of interest to identify one or more conditions of mucus therein, the model trained using a plurality of images having varying conditions of mucus, wherein output of the model includes at least a grade corresponding to an amount of mucus present in the one or more regions of interest;
- based at least in part on the output of the model, predicting a health characteristic of an animal from which the biological sample originated without laboratory analysis of the biological sample; and
- presenting the health characteristic to a user associated with the animal.

20. A system for analyzing an image of a biological sample to provide a health assessment of an animal, the system comprising:
- a data network;
- a smartphone coupled to the data network; and
- a remote computing resource coupled to the data network and accessible to the smartphone through the data network, the remote computing resource including a processor and a memory, the memory storing code executable by the processor to perform the steps of:
  - receiving an image taken from a camera of the smartphone over the data network, the image including a biological sample containing mucus;
  - identifying and extracting one or more regions of interest within the image for further analysis;
  - applying a model to the one or more regions of interest to identify one or more conditions of mucus therein, the model trained using a plurality of images having varying conditions of mucus, wherein output of the model includes at least a grade corresponding to an amount of mucus present in the one or more regions of interest;
  - based at least in part on the output of the model, predicting a health characteristic of an animal from which the biological sample originated without laboratory analysis of the biological sample; and
  - presenting the health characteristic on the smartphone.

* * * * *